United States Patent [19]

Gardner

[11] Patent Number: 5,257,862
[45] Date of Patent: Nov. 2, 1993

[54] MIXER-WASHER APPARATUS

[76] Inventor: Carl Gardner, 1436 E. 355 St., East Lake, Ohio 44095

[21] Appl. No.: 51,996

[22] Filed: Apr. 26, 1993

[51] Int. Cl.$^5$ .............................................. B01F 13/06
[52] U.S. Cl. ................................... 366/139; 366/138; 366/249; 366/601; 366/602
[58] Field of Search ............... 366/139, 138, 208, 209, 366/212, 213, 240, 241, 244, 245, 249, 251, 250, 279, 601, 602, 605

[56] References Cited

U.S. PATENT DOCUMENTS

| | | | |
|---|---|---|---|
| 1,847,227 | 3/1932 | Ringwald | 366/288 |
| 2,696,022 | 12/1954 | Steinbock . | |
| 2,973,187 | 2/1961 | Wehmer . | |
| 3,263,970 | 8/1966 | Steinbock | 366/279 |
| 3,557,411 | 1/1971 | Ravasi | 222/152 |
| 3,640,510 | 2/1972 | Lea | 366/139 |
| 4,547,076 | 10/1985 | Maurer | 366/244 |
| 4,798,471 | 1/1989 | Laempe | 366/244 |
| 4,854,716 | 8/1989 | Ziemann | 366/139 |
| 4,984,620 | 1/1991 | Assfalg | 366/139 |

Primary Examiner—Robert W. Jenkins
Attorney, Agent, or Firm—Arthur L. Wolfe

[57] ABSTRACT

An automatic vacuum mixer-washer apparatus is described. In this apparatus, a mixing vessel moves automatically from load-unload position to mix-wash position and back to the load-unload position after completing either the mixing cycle or the washing cycle. The mixing means connects automatically to the driving means, thereby activating a timer to control the duration of the mixing and washing cycles. This vacuum mixer-washer apparatus is especially useful for mixing dental materials under vacuum and automatically washing the mixing means after removing said mixed dental materials.

44 Claims, 14 Drawing Sheets

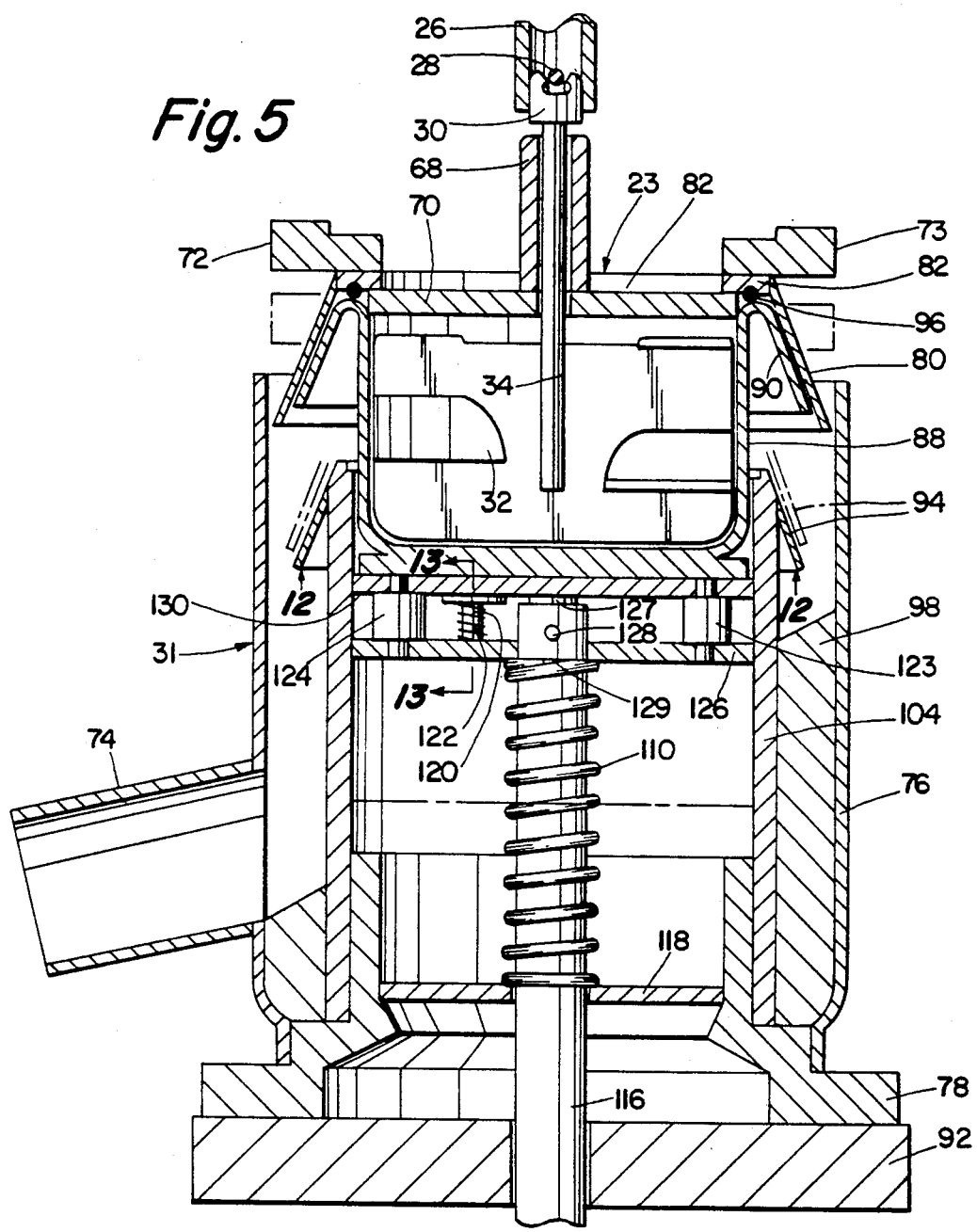

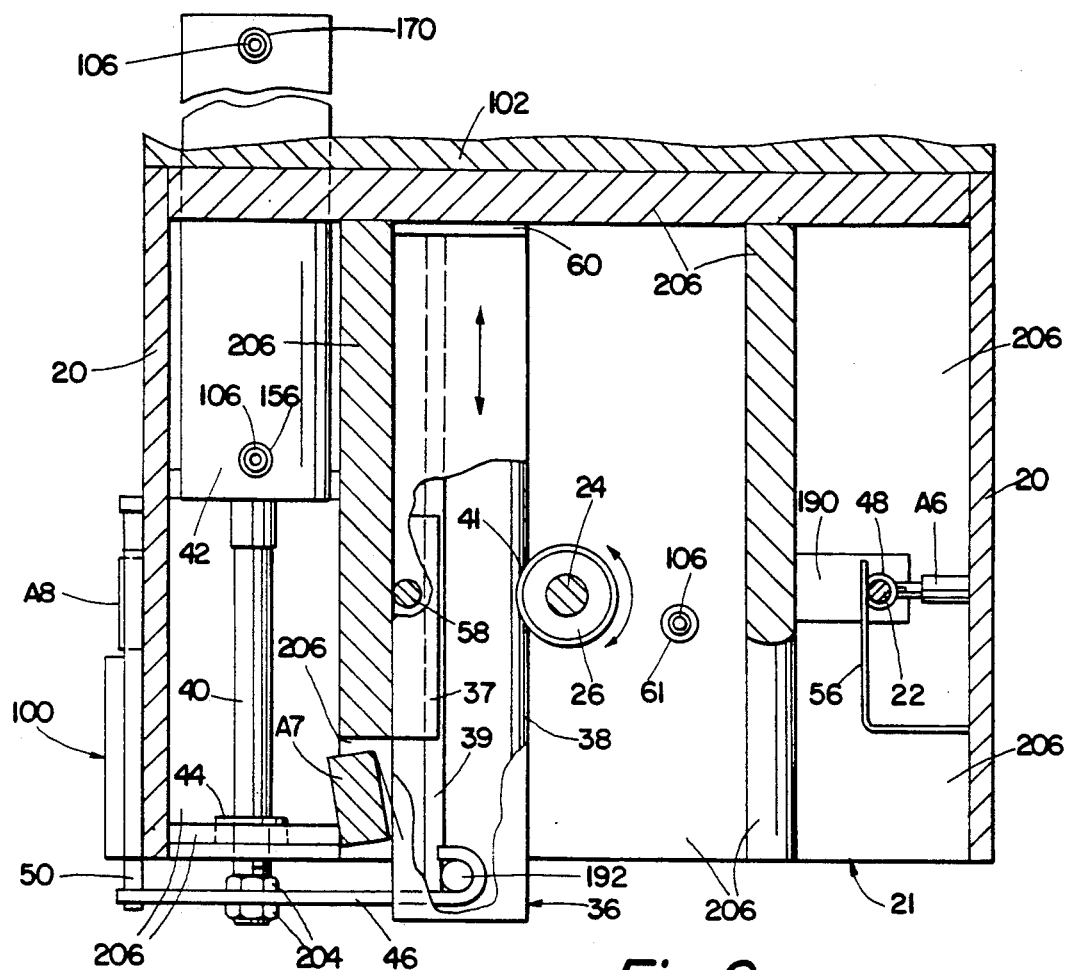
Fig. 9
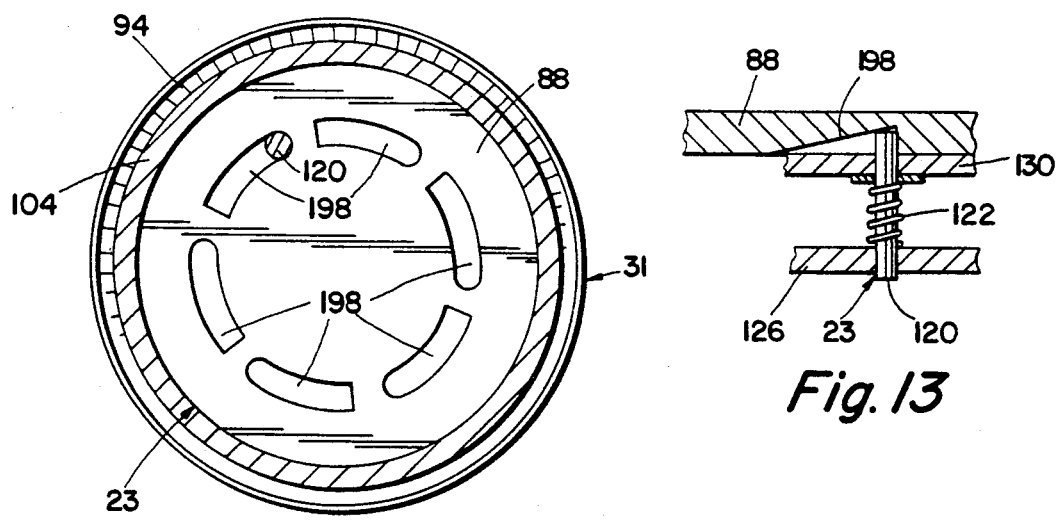
Fig. 12
Fig. 13

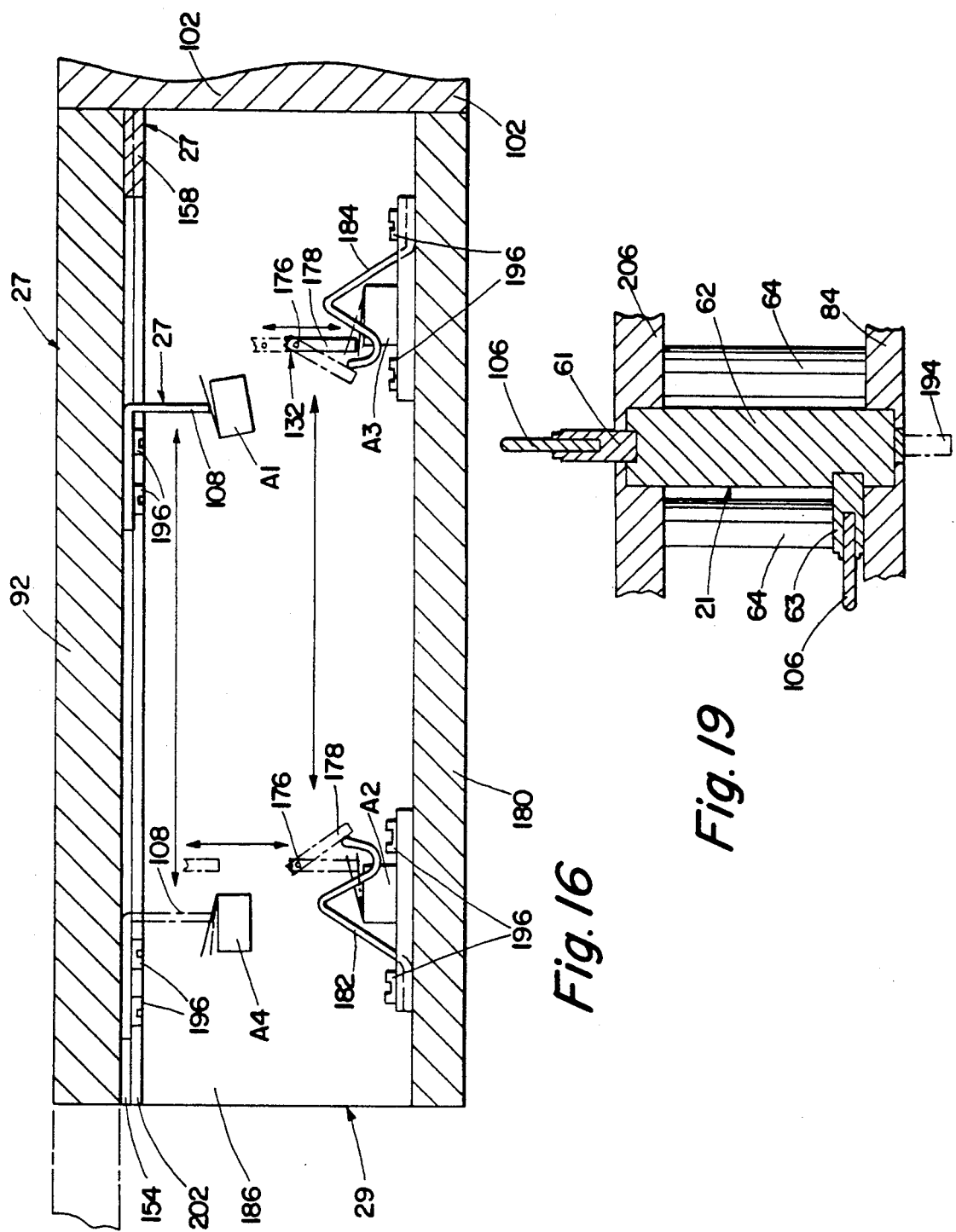

MIXER-WASHER APPARATUS

BACKGROUND OF THE INVENTION

1. Field of the Invention

This invention relates to a mixer-washer apparatus and more particularly, to a powered mixer-washer apparatus that holds a mixing vessel mechanically, that attaches said mixing vessel to a mixer motor semi-automatically or automatically, that mixes a variety of materials with or without application of vacuum semi-automatically or automatically, and that washes said mixing vessel semi-automatically or automatically.

2. Description of the Prior Art

Power mixers are old and well known but have generally been of the type requiring manual washing or cleaning of a mixing vessel after the materials have been mixed in, and removed from, said mixing vessel. Such washing or cleaning is a tedious, time-consuming job and generally, it is difficult to clean all the surfaces thoroughly by hand. Moreover, it is extremely hazardous for one to wash or clean a mixing vessel that had been used to mix chemicals, drugs, radioactive materials, or other toxic compounds. Furthermore, many materials used in preparing models or molds, harden quickly after mixing, requiring one to pour the mixture into the mold or to form a mold as soon as possible, thereby not permitting time to wash or clean the mixing vessel before using the mixed materials. It is highly advantageous to have an automatic or semi-automatic mixer-washer to enable one to mix rapidly and to wash the mixing vessel while one is working with castings, molds or models.

Typical examples of mixing devices commonly used heretofore and at present are described in U.S. Pat. No. 1,847,227, mixing and agitating machine for drinks or food; U.S. Pat. No. 3,263,970, power mixer with motor started automatically when parts are assembled; U.S. Pat. No. 3,358 973, mixing apparatus for mixing asphalt, concrete and the like; U.S. Pat. No. 4,095,288, variable agitator mixer or washer. However, none of these patents describe mixing and washing as described in the present invention.

Patents that describe vacuum mixing devices include U.S. Pat. Nos. 2,453,914; 2,696,022; 2,777,177; 2,973,187; 3,139,270; 3,358,971; 3,557,411; 3,640,510. U.S. Pat. No. 3,640,510 describes a vacuum stirring device which has a time switch to determine the duration of mixing. However, none of the cited patents describe vacuum mixing and washing with the automatic or semi-automatic features described in the present invention. U.S. Pat. Nos. 2,696,022 and 2,777,177 describe an investment mixer in which a vacuum is established during the mixing and subsequent casting operation; however, no washing of the mixing vessel after completing the mixing and casting operations is claimed.

SUMMARY OF THE INVENTION

The objects of the invention include:

First, the provision of apparatus of various sizes for automatic or semi-automatic mixing of a wide range of materials in composition, particle size and volume.

Second, the provision of means for applying vacuum before, or at the start of mixing if desired.

Third, the provision of a means for positioning a mixing vessel, either automatically or semi-automatically, in preparation for mixing or washing, and after said mixing or washing.

Fourth, the provision of a means for positioning a driving means and/or a mixing means.

Fifth, the provision of a means for controlling accurately the duration of mixing or washing.

Sixth, the provision of means for washing dirty mixing vessels, automatically or semi-automatically.

Seventh, the provision of means for mixing materials and washing dirty mixing vessels with less labor and lower cost.

Eighth, to save time because the washing operating can be performed immediately after emptying mixed ingredients, without disconnecting the tubing from the lid of the mixing vessel.

Ninth, the provision of apparatus for mixing and washing that will pay for itself within a short period of time by allowing an operator to work more efficiently.

Tenth, the provision of apparatus that is simple to operate.

With the above mentioned and other objects in view, the invention consists in the useful and novel provision, construction, association, and relative arrangement of parts, members and features, as shown in certain embodiments in the accompanying drawings, described generally, and more particularly pointed out in the claims.

Other objects and advantages of the present invention should be readily apparent by referring to the following specification considered in conjunction with the accompanying drawings forming a part thereof and it is to be understood that modifications may be made in the structural details there shown and described, within the scope of the appended claims, without departing from or exceeding the spirit of the invention.

Among the different embodiments of the invention, particularly advantageous is the one wherein an operator puts the materials in a mixing vessel and then places said mixing vessel in the load-unload position of said apparatus. The operator then presses a switch, thereby starting the automatic mixing cycle, namely first, transporting the mixing vessel and lid to the mix-wash position; second, mixing the materials for a designated period of time; and third, returning said mixing vessel and lid to the load-unload position. After the operator unloads the well-mixed materials from the mixing vessel, said operator again places the mixing vessel in the load-unload position, presses the same switch as before, thereby starting the automatic washing cycle, wherein, first, the mixing vessel and lid move into position as described before; second, water enters through tubing and is forced to leave between said lid and said mixing vessel while the motor is running, thereby creating agitation and turbulence and cleaning the inner surface of said mixing vessel and lid; third, air enters said mixing vessel, thereby purging water from the tubing and forcing water agitated by the rotating paddle out of the mixing vessel at the end of the cleaning operation; and fourth, the mixing vessel and lid move back into the load-unload position.

In another embodiment of the invention, semi-automatic mixing-washing cycles are used, thereby enabling manufacture of the mixing-washing apparatus at lower cost than for the automatic vacuum mixer-washer apparatus. The difference between the automatic and semi-automatic apparatus is that in using the semi-automatic apparatus, the operator moves the mixing vessel and lid from the load-unload position to the mix-wash position and back to the load-unload position for both the mixing and washing operations instead of the said movements being performed automatically as described previously.

BRIEF DESCRIPTION OF THE DRAWINGS

FIG. 5 is a sectional view, as seen from line 5—5 on FIG. 10, showing mixer-washer assembly 23 and container assembly 31, and also showing a sectional view of socket 26 and socket pin 28.

FIG. 6 is a bottom view of connector 30.

FIG. 7 is a side view of connector 30.

FIG. 8 is a side view of connector 30, rotated 90 degrees from the view shown in FIG. 7.

FIG. 9 is a sectional view as seen from line 9—9 in FIG. 2.

FIG. 12 is a sectional view as seen from line 12—12 in FIG. 5.

FIG. 13 is a sectional view as seen from line 13—13 in FIG. 5, showing the top of no-spin pin 120 extending through discoid vessel support 130 and touching recessed vessel surface 198 in mixing vessel 88.

FIG. 16 is a sectional view, as seen from line 16—16 in FIG. 2.

FIG. 19 is a side sectional view, as seen from line 19—19 on FIG. 2, showing fitting 61, lid push cylinder 62, fitting 63, spacer 64, lid hold 84, tubing 106, lid push rod 194, and frame 206.

DESCRIPTION OF THE PREFERRED EMBODIMENTS

In the several views of the drawings, similar reference materials are employed to denote the same or similar parts except when necessary to distinguish similar parts.

Figure 1:
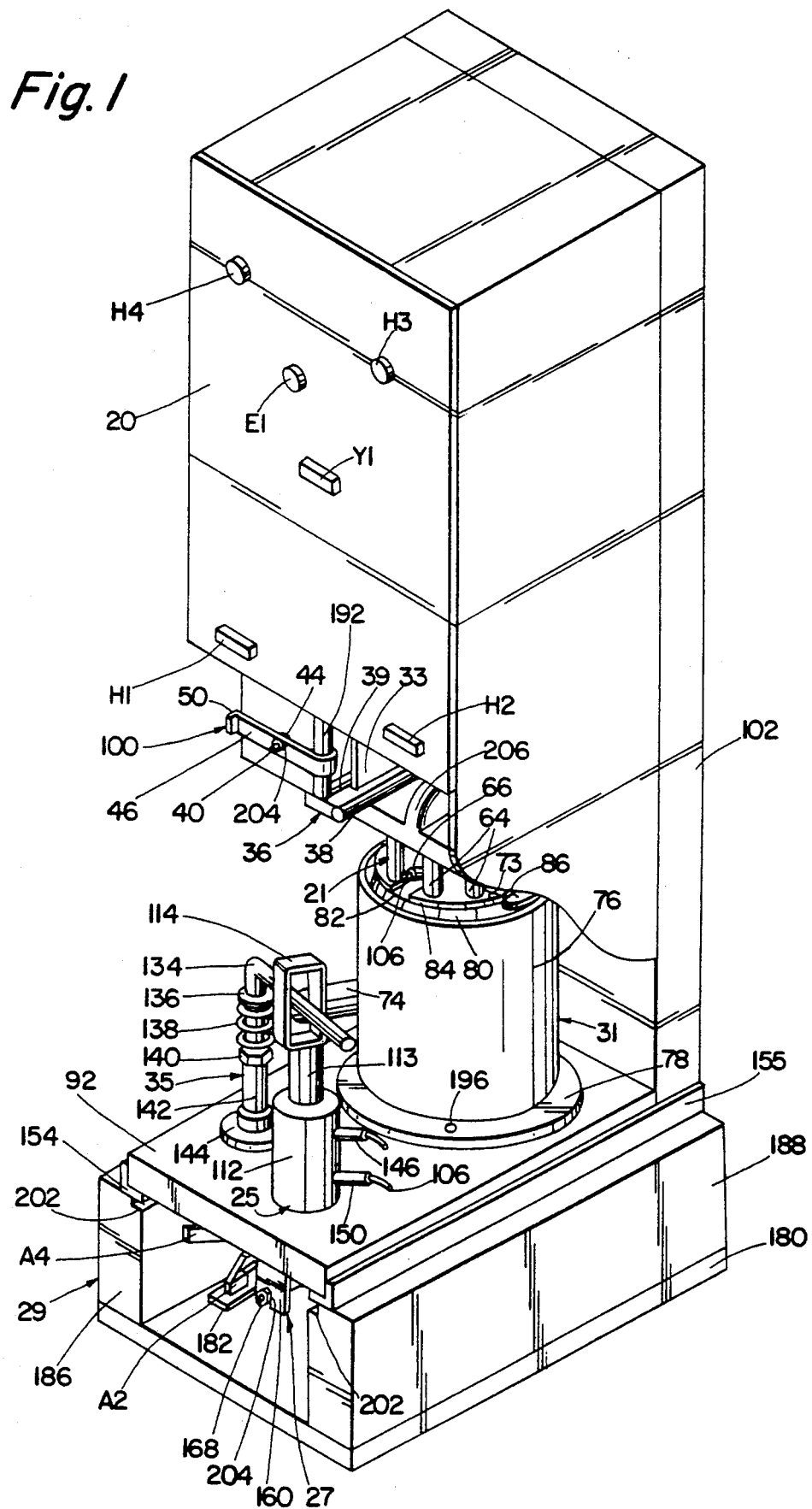
FIG. 1 is a perspective view of the invention from the upper right front.
Figure 2:
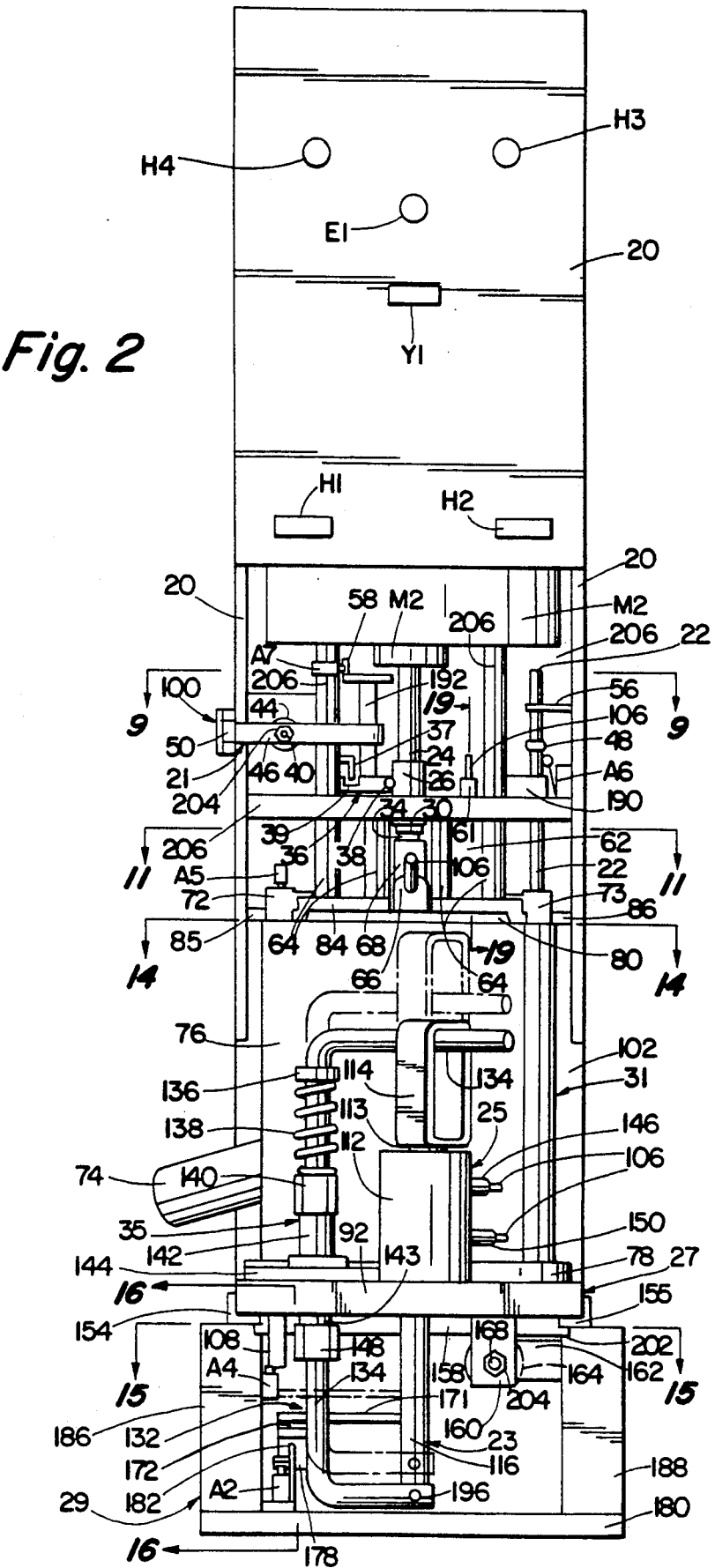
FIG. 2 is an elevational view from the front of the invention showing structural details. Lines 9—9, 11—11, 14—14, 15—15, 16—16 and 19—19 indicate sections of the invention illustrated in FIGS. 9, 11, 14, 15, 16 and 19, respectively. Driving motor M2, used for both mixing and washing, is shown.
Figure 18A:
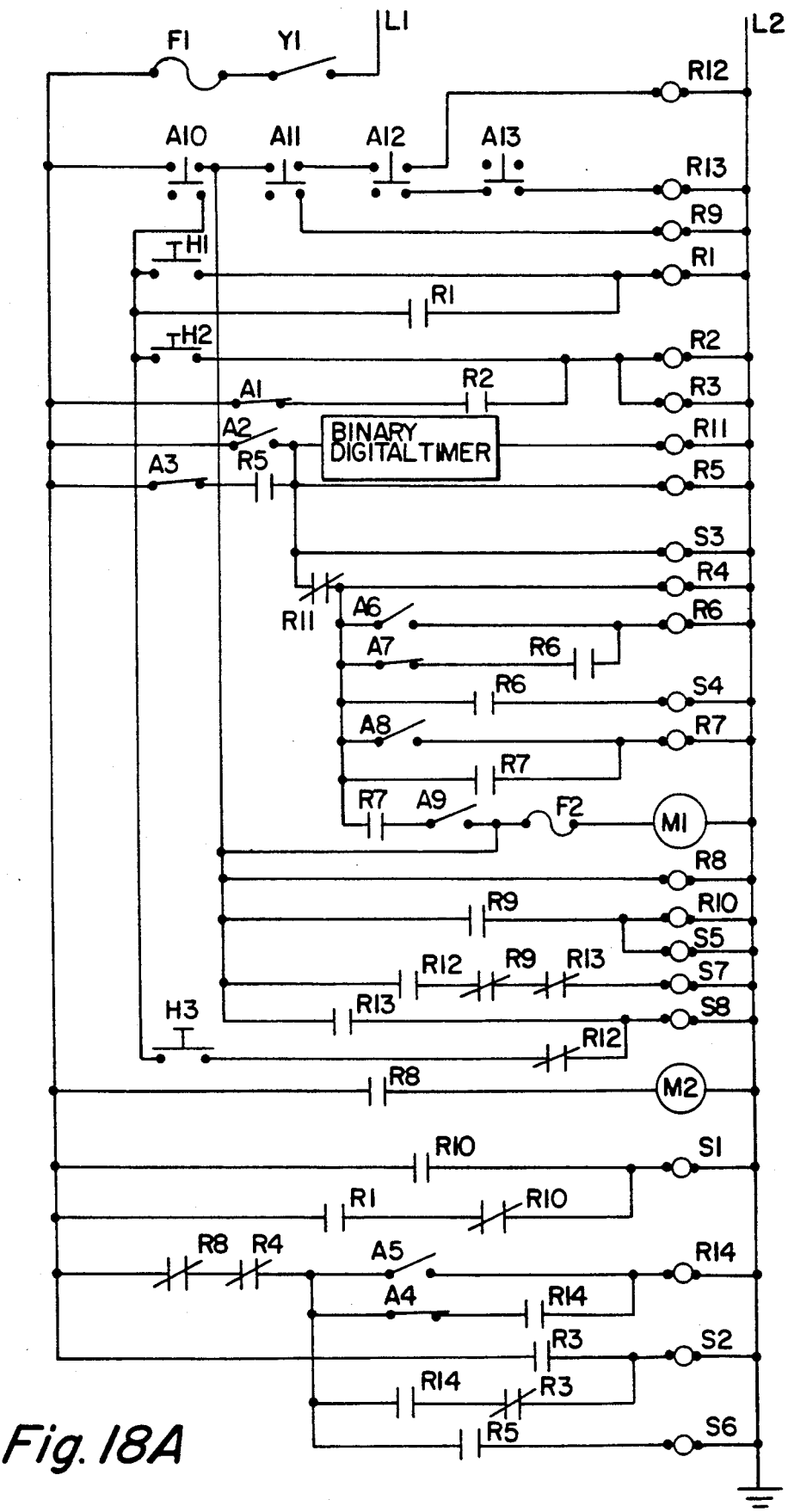
FIG. 18A is a schematic wiring diagram of an embodiment of the automatic vacuum mixer-washer apparatus of the present invention that includes socket spinner assembly 36.

Referring to FIGS. 1 and 2, one sees that the mixer-washer apparatus comprising the present invention includes housing 20, support 102, left rail 154, right rail 155, base 180, left rail support 186, right rail support 188, and frame 206, which may be made from any suitable material, such as metal, synthetic resin (plastic), or the like, and includes AC driving motor M2 of appropriate size and horsepower, which is used to operate paddle 32 of said automatic vacuum mixer-washer apparatus (cf. FIG. 18A). Electricity powers said driving motor M2; however, one could use other types of motors, such as pneumatic or the like. Housing 20, base 180, left rail support 186, right rail support 188, frame 206 and driving motor M2 attach to support 102.

Housing 20 holds suitable instrumentation for operating the present invention and provides aesthetic enhancement, and protection from electrical shock or other injury.

Left rail 154, fixedly attached to left rail support 186 and right rail 155, fixedly attached to right rail support 188, support and passively guide Carriage 92. Said Carriage 92 is a part of carriage Assemblage, and is also referred to as conveyance means. other methods of guidance, well known by skilled machinists, could be used, such as rollers, grooves and the like.

A list of reference numerals used in FIGS. 1–19 follows, along with the names of the associated parts.

|    | Part Name                |
|----|--------------------------|
| 20 | Housing                  |
| 22 | Spin pin                 |
| 24 | Motor shaft              |
| 26 | Socket                   |
| 28 | Socket pin               |
| 30 | Connector                |
| 32 | Paddle                   |
| 33 | Spacer                   |
| 34 | Paddle shaft             |
| 37 | Spinner hold             |
| 38 | Spin strip               |
| 39 | Recessed spinner surface |
| 40 | Spin rod                 |
| 41 | Arcuate recessed surface |
| 42 | Spin cylinder            |
| 44 | Spin bearing             |
| 46 | Arm                      |
| 48 | Protuberance             |

-continued

| | Part Name |
|---|---|
| 50 | Strip |
| 52 | Trigger |
| 54 | Trigger pin |
| 56 | Guide |
| 58 | Spin deactivator |
| 60 | Bumper |
| 61 | Fitting |
| 62 | Lid-push cylinder |
| 63 | Fitting |
| 64 | Spacer |
| 66 | Conduit |
| 68 | Bearing and bearing housing with seal |
| 70 | Lid |
| 72 | Left wing flange |
| 73 | Right wing flange |
| 74 | Flow pipe |
| 76 | Container |
| 78 | Flange |
| 80 | Lid apron flange |
| 82 | Lid flange |
| 84 | Lid hold |
| 85 | Left guide stop |
| 86 | Right guide stop |
| 88 | Mixing vessel |
| 90 | Vessel apron flange |
| 92 | Carriage |
| 94 | Cylinder apron flange |
| 96 | O-ring |
| 98 | Channel base |
| 102 | Support |
| 104 | Mixer cylinder |
| 106 | Tubing |
| 108 | Deactivator |
| 110 | Push spring |
| 112 | Up-down cylinder |
| 113 | Up-down rod |
| 114 | Free-play unit |
| 116 | Pull-push bar |
| 118 | Discoid pressure plate |
| 120 | No-spin pin |
| 122 | No-spin spring |
| 123 | Shoulder pin |
| 124 | Shoulder pin |
| 125 | Shoulder pin |
| 126 | Discoid pressure plate |
| 127 | Shoulder pin |
| 128 | Compression pin |
| 129 | Compression pin |
| 130 | Discoid vessel support |
| 134 | Pressure-transfer bar |
| 136 | Spring stop |
| 138 | Bar spring |
| 140 | Top bearing |
| 142 | Top pipe |
| 143 | Bottom pipe |
| 144 | Flange |
| 146 | Fitting |
| 148 | Bottom bearing |
| 150 | Fitting |
| 152 | Fitting |
| 153 | Fitting |
| 154 | Left rail |
| 155 | Right rail |
| 156 | Fitting |
| 158 | Under-rail bar |
| 160 | Cylinder-attaching bracket |
| 162 | Cylinder bracket |
| 164 | In-out cylinder |
| 168 | In-out rod |
| 170 | Fitting |
| 171 | Extension |
| 172 | Holder |
| 174 | Spring |
| 176 | Shaft |
| 178 | Plate |
| 180 | Base |
| 182 | Bumper guide |
| 184 | Bumper guide |
| 186 | Left rail support |
| 188 | Right rail support |

-continued

| | Part Name |
|---|---|
| 190 | Protuberance stop |
| 192 | Pull pin |
| 194 | Lid push rod |
| 196 | Bolt |
| 198 | Recessed vessel surface |
| 200 | Set screw |
| 202 | Recessed groove surface |
| 204 | Nut |
| 206 | Frame |

The mixer-washer apparatus comprising the present invention utilizes the following assemblies (the figures illustrating these assemblies are also listed):

| Assemblies | Figures |
|---|---|
| Connect-disconnect assembly 21 | 11, 9, 19, 3A, 3B |
| Mixer-washer assembly 23 | 5, 14 |
| Vertical assembly 25 | 2, 14, 1 |
| Carriage assembly 27 | 15, 2, 16 |
| Horizontal assembly 29 | 15, 16, 2 |
| Container assembly 31 | 5, 10 |
| Pressure-transfer assembly 35 | 1, 2, 3B, 14, 15 |
| Socket spinner assembly 36 | 9, 1, 2, 3A |
| Timer activator 100 | 4, 9 |
| Activator-deactivator 132 | 17, 16, 2, 15 |

Carriage Assemblage

Assemblies 23, 25, 27, 31, 35 and 132 (see above) comprise the carriage assemblage. The carriage assemblage moves as a unit, thereby locating mixing vessel 88, lid 70 and tubing 106 attached to said lid 70 in two appropriate positions; namely, the load-unload position (cf. FIG. 3B) and the mix-wash position (cf. FIGS. 1 and 3A).

Each assembly comprises the following parts (included are Figures and where they are illustrated).

| Connect-Disconnect Assembly 21 | | |
|---|---|---|
| Part Name | Part Numeral | Figure |
| Switch | A5 | 2, 18A, 18B, 11 |
| Switch | A6 | 2, 9, 18A, 18B |
| Switch | A7 | 2, 9, 18A |
| Switch | A8 | 9, 18A |
| Switch | A9 | 11, 18A |
| Spin pin | 22 | 2, 3B, 11 |
| Motor shaft | 24 | 2, 9 |
| Socket | 26 | 2, 9 |
| Socket pin | 28 | 5 |
| Spinner-hold | 37 | 2 |
| Spin rod | 40 | 1, 2, 3A, 3B, 9 |
| Spin cylinder | 42 | 9 |
| Spin bearing | 44 | 2, 9 |
| Arm | 46 | 1, 2, 3A, 3B, 9 |
| Protuberance | 48 | 2, 9 |
| Guide | 56 | 2, 9 |
| Spin deactivator | 58 | 2, 9 |
| Fitting | 61 | 2, 9, 19 |
| Lid-push cylinder | 62 | 2, 11, 19 |
| Fitting | 63 | 19 |
| Spacer | 64 | 2, 11, 19 |
| Lid-hold | 84 | 2, 3B, 11, 19 |
| Left guide stop | 85 | 2, 11 |
| Right guide stop | 86 | 2, 11, 3B |
| Tubing | 106 | 2, 11 |
| Fittings | 156, 170 | 9 |
| Protuberance stop | 190 | 2, 9 |
| Lid push rod | 194 | 19 |
| Nut | 204 | 1, 2, 3A, 3B, 9 |
| Frame | 206 | 1, 2, 9 |

| Mixer-Washer Assembly 23 | | |
|---|---|---|
| Part Name | Part Numeral | Figure |
| Connector | 30 | 2, 5, 6, 7, 8, 10, 11 |
| Paddle | 32 | 5 |
| Paddle shaft | 34 | 5 |
| Conduit | 66 | 2, 10, 11 |
| Bearing and bearing house with seal | 68 | 2, 5, 10, 11 |
| Lid | 70 | 5, 10 |
| Left wing flange | 72 | 2, 5, 10, 11 |
| Right wing flange | 73 | 2, 3A, 5, 10, 11, 1 |
| Lid apron flange | 80 | 5, 10, 11 |
| Lid flange | 82 | 5, 10, 11 |
| Mixing vessel | 88 | 5, 12 |
| Vessel apron flange | 90 | 5 |
| O-ring | 96 | 5 |
| Tubing | 106 | 10, 11 |
| Push spring | 110 | 5 |
| Pull-push bar | 116 | 5 |
| No-spin pin | 120 | 5, 13, 14 |
| No-spin spring | 122 | 5, 13 |
| Shoulder pins | 123, 124, 125, 127 | 5, 14 |
| Discoid pressure plate | 126 | 5 |
| Compression pins | 128, 129 | 5 |
| Discoid vessel support | 130 | 5, 14 |
| Bolt | 196 | 1, 15 |
| Recessed vessel surface | 198 | 12, 13 |

| Vertical Assembly 25 | | |
|---|---|---|
| Part Name | Part Numeral | Figure |
| Up-down cylinder | 112 | 1, 2, 3A, 3B, 14 |
| Up-down rod | 113 | 1, 2, 3A, 3B |
| Free-play unit | 114 | 1, 2, 3A, 3B, 14 |
| Tubing | 106 | 1 |
| Fittings | 146, 150 | 1, 2, 3A, 3B |

| Carriage Assembly 27 | | |
|---|---|---|
| Part Name | Part Numeral | Figure |
| Carriage | 92 | 1, 2, 3A, 3B, 5, 10, 11, 14, 16 |
| Deactivator | 108 | 2, 15, 16 |
| Under-rail bar | 158 | 2, 15, 16 |
| Cylinder-attaching bracket | 160 | 1, 2, 15 |
| Bolt | 196 | 15 |

| Horizontal Assembly 29 | | |
|---|---|---|
| Part Name | Part Numeral | Figure |
| Switch | A1 | 15, 16 |
| Switch | A2 | 15, 16 |
| Switch | A3 | 15, 16 |
| Switch | A4 | 15, 16 |
| Fittings | 152, 153 | 15 |
| Left rail | 154 | 1, 2, 16 |
| Right rail | 155 | 1, 2, 3A, 3B |
| Cylinder bracket | 162 | 15 |
| In-out cylinder | 164 | 2, 15 |
| In-out rod | 168 | 1, 2, 3B |
| Base | 180 | 1, 2, 3A, 3B, 15, 16 |
| Bumper guides | 182, 184 | 1, 2, 16 |
| Left rail support | 186 | 1, 2, 15, 16 |
| Right rail support | 188 | 1, 2, 3A, 3B, 15 |
| Bolt | 196 | 15, 16 |
| Recessed groove surface | 202 | 1, 2, 15, 16 |
| Nut | 204 | 1, 2, 15 |

| Container Assembly 31 | | |
|---|---|---|
| Part Name | Part Numeral | Figure |
| Flow pipe | 74 | 1, 5, 10, 11 |
| Container | 76 | 1, 5, 10, 11 |
| Flange | 78 | 1, 5, 10, 11 |
| Cylinder apron flange | 94 | 5, 12, 14 |
| Channel base | 98 | 5, 10, 11, 14 |
| Mixer cylinder | 104 | 5, 12, 14 |
| Discoid pressure plate | 118 | 5 |
| Bolt | 196 | 10, 11 |

| Pressure-Transfer Assembly 35 | | |
|---|---|---|
| Part Name | Part Numeral | Figure |
| Pressure-transfer bar | 134 | 1, 2, 3A, 3B, 14, 15 |
| Spring stop | 136 | 1, 2, 3A, 3B |
| Bar spring | 138 | 1, 2, 3A, 3B |
| Top bearing | 140 | 1, 2, 3A, 3B |
| Top pipe | 142 | 1, 2, 3A, 3B |
| Flange | 144 | 1, 2, 3A, 3B, 14 |
| Bottom pipe | 143 | 2, 3B, 15 |
| Bottom bearing | 148 | 2, 15 |
| Bolt | 196 | 2, 14 |
| Set screw | 200 | 14 |
| Nut | 204 | 15 |

| Socket-Spinner Assembly 36 | | |
|---|---|---|
| Part Name | Part Numeral | Figure |
| Spacer | 33 | 1, 3A |
| Spin strip | 38 | 1, 2, 3A, 3B, 9 |
| Recessed spinner surface | 39 | 1, 2, 9 |
| Bumper | 60 | 9 |
| Pull pin | 192 | 1, 2, 3A, 3B, 9 |
| Nut | 204 | 1, 2, 3A, 3B, 9 |

| Timer-Activator 100 | | |
|---|---|---|
| Part Name | Part Numeral | Figure |
| Strip | 50 | 1, 2, 4, 9 |
| Trigger | 52 | 4 |
| Trigger pin | 54 | 4 |
| Switch | A8 | 4, 9 |

| Activator-Deactivator 132 | | |
|---|---|---|
| Part Name | Part Numeral | Figure |
| Extension | 171 | 2, 15, 17 |
| Holder | 172 | 2, 15, 17 |
| Spring | 174 | 15, 17 |
| Shaft | 176 | 16, 17 |
| Plate | 178 | 2, 16, 17 |

Figure 18B:
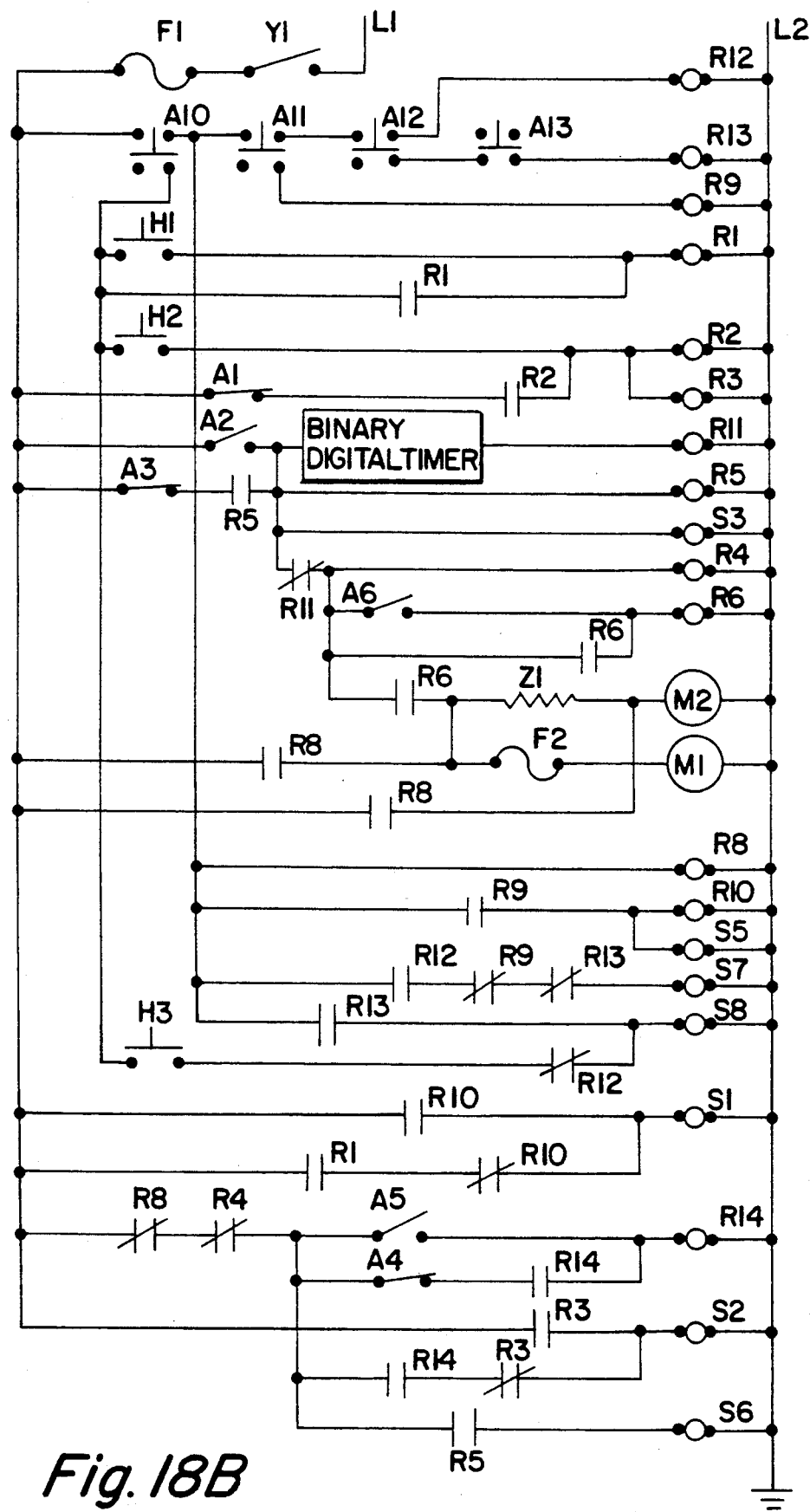
FIG. 18B is a schematic wiring diagram of a preferred embodiment of the automatic vacuum mixer-washer apparatus of the present invention.

A list of solenoid valves, their reference numerals, description and control function, follows (also see FIG. 18B).

| Designation | Description | Control |
|---|---|---|
| S1 | 2-way, direct acting normally closed valve | Vacuum transducer pump |
| S2 | 4-way, directional air valve, pilot operated | Up-down cylinder 112 |
| S3 | 4-way, directional air valve, pilot operated | In-out cylinder 164 |
| S4 | 4-way, directional air valve, pilot operated | Spin cylinder 42 |
| S5 | 2-way, direct acting, normally | Vacuum reserve |

-continued

| Designation | Description | Control |
| --- | --- | --- |
| | closed valve | |
| S6 | 4-way, directional air valve, pilot operated | Lid-push cylinder 62 |
| S7 | 2-way, internal pilot-operated, diaphragm type, normally closed valve | Water |
| S8 | 2-way, direct acting, normally closed valve | Air |
| S9 | 2-way, direct acting, normally closed valve | Atmosphere |

All solenoid valves, S1-S9, are available commercially; other suitable types of solenoid valves may be used. Each letter S preceded by a circle in FIGS. 18A, 18B, 18C, 18D and 18E represents a solenoid valve. Each said circle represents the coil of each said solenoid valve.

When solenoid valves S2, S3, S4 and S6 activate, the rods in the respective cylinders move in one direction, and when the solenoid valves deactivate, the rods move in the opposite direction.

Manually-adjustable, commercially-available meters moderate the rate of movement of the rods in spin cylinder 42, up-down cylinder 112 and in-out cylinder 164.

E1 is an LED light that indicates drainage of liquid from tubing 106 and from solenoid valves S5, S7 and S8 (cf. FIGS. 18c and 18E). switch H4 starts the drainage by opening solenoid valve S8. Either switch H2 or Y1 will close said solenoid valve S8 (cf. FIG. 1 also).

Manually-adjustable, commercially-available air pressure gauges control the maximum amount of air pressure allowed into each said cylinder and lid-push cylinder 62.

The mixer-washer apparatus of the present invention is generally constructed so that the paddle shaft is in essentially vertical position during the mixing and washing cycles. However, said apparatus could also be made so that the paddle shaft is purposely tilted at an angle, or even be horizontal, in order to, for example, obtain better mixing or make for easier washing.

A description of switches and relays follows (cf. FIG. 18A).

| Switch | Use |
| --- | --- |
| A1 | Single-pole, single-throw, spring return normally closed (n.c.) lever |
| A2 | Single-pole, single-throw, spring return normally open (n.o.) lever |
| A3 | Single-pole, single-throw, spring return n.c. lever |
| A4 | Single-pole, single-throw, spring return n.c. lever |
| A5 | Single-pole, single-throw, spring return n.o. lever |
| A6 | Single-pole, single-throw, spring return n.o. roller lever |
| A7 | Single-pole, single-throw, spring return n.c. lever |
| A8 | Single-pole, single-throw, spring return n.o. lever |
| A9 | Single-pole, single-throw, spring return n.o. roller lever |
| A10 | Single-pole, double-throw, spring return roller lever (cam switch) |
| A11 | Single-pole, double-throw, spring return roller lever (cam switch) |
| A12 | Single-pole, double-throw, spring return roller lever (cam switch) |
| A13 | Single-pole, double-throw, spring return roller lever (cam switch) |
| H1 | Single-pole, single-throw, n.o., push-button, momentary |
| H2 | Single-pole, single-throw, n.o., push-button, momentary |
| H3 | Single-pole, single-throw, n.o., push-button, momentary |
| H4 | Single-pole, single-throw, n.o., push-button, momentary |
| Y1 | Single-pole, single-throw, on-off, rocker switch |

FIGS. 18A, 18B, 18C, 18D and 18E are wiring schematics to illustrate and be useful; however, one skilled in the art could modify the wiring details, in the embodiments described in said wiring schematics, within the scope of the appended claims, without departing from or exceeding the spirit of the invention.

All the above switches are available commercially; other types of switches can be used to perform the same function.

Cam timer-motor M1 turns cams that operate switches A10, A11, A12 and A13 at the appropriate times.

Switches A1-A13 are all single-pole, double-throw switches; some are used as single-throw switches, normally closed or normally open, according to which two of three posts are connected to the circuits.

All relays are double-pole, double-throw relays (D.P.D.T.). Each letter R preceded by a circle in FIGS. 18A, 18B, 18C, 18D and 18E represents a relay. Each said circle represents the coil of said relay.

In FIGS. 18A, 18B, 18C, 18D and 18E, each letter R that is to the left of the circles represents the adjacent relay contacts. The number following said letter R indicates the numbered relay in which said contacts are an integral part.

Figure 3A:
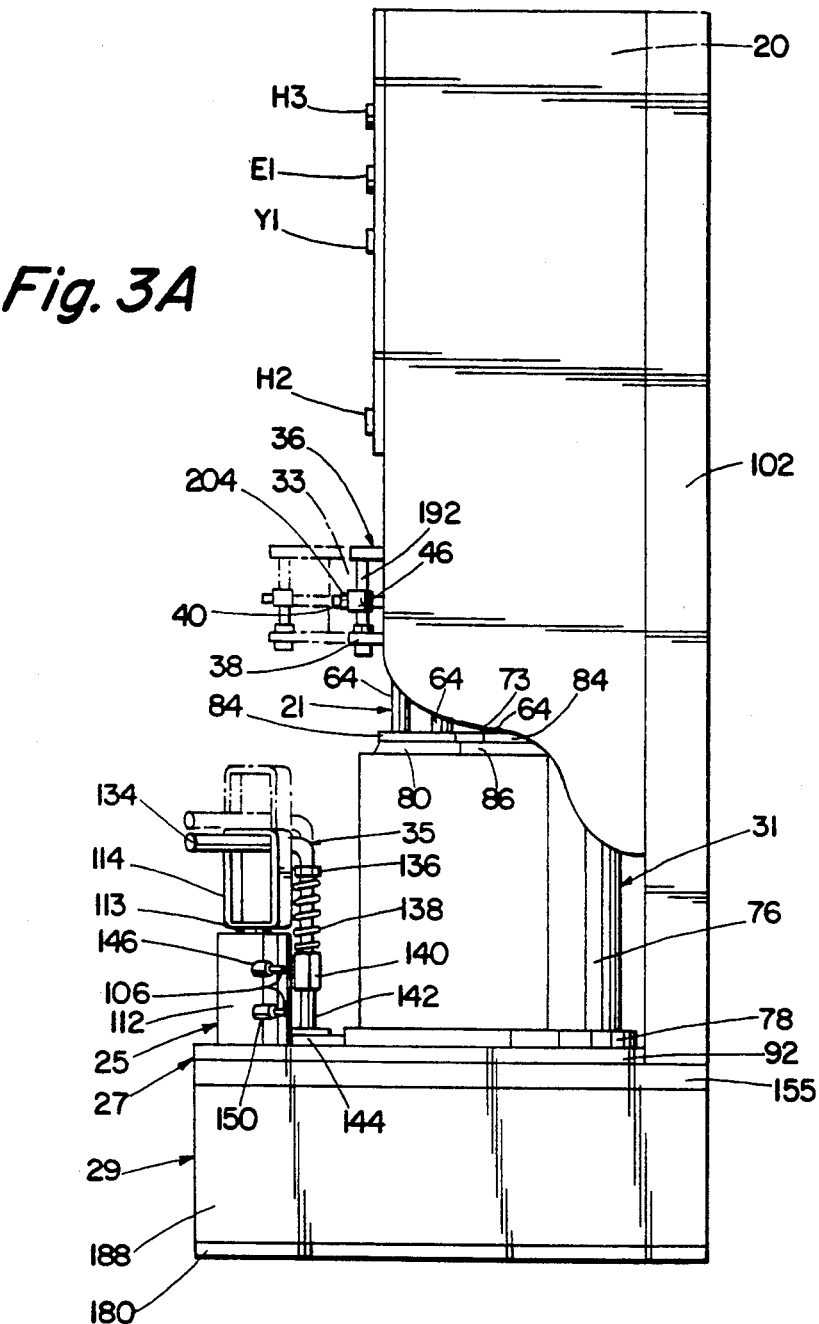
FIG. 3A is an elevational view of the right side of the invention showing the apparatus in the in-down position, with the lower phantoms showing the positions of various parts when the apparatus is in the mix-wash position.

FIGS. 2 and 3A, in the phantom views, illustrate the relative position of free-play unit 114 and the upper horizontal portion of pressure-transfer bar 134 when the carriage assemblage (see page 9, lines 17 through 22) is in position for mixing operations and for washing operations.

Figure 3B:
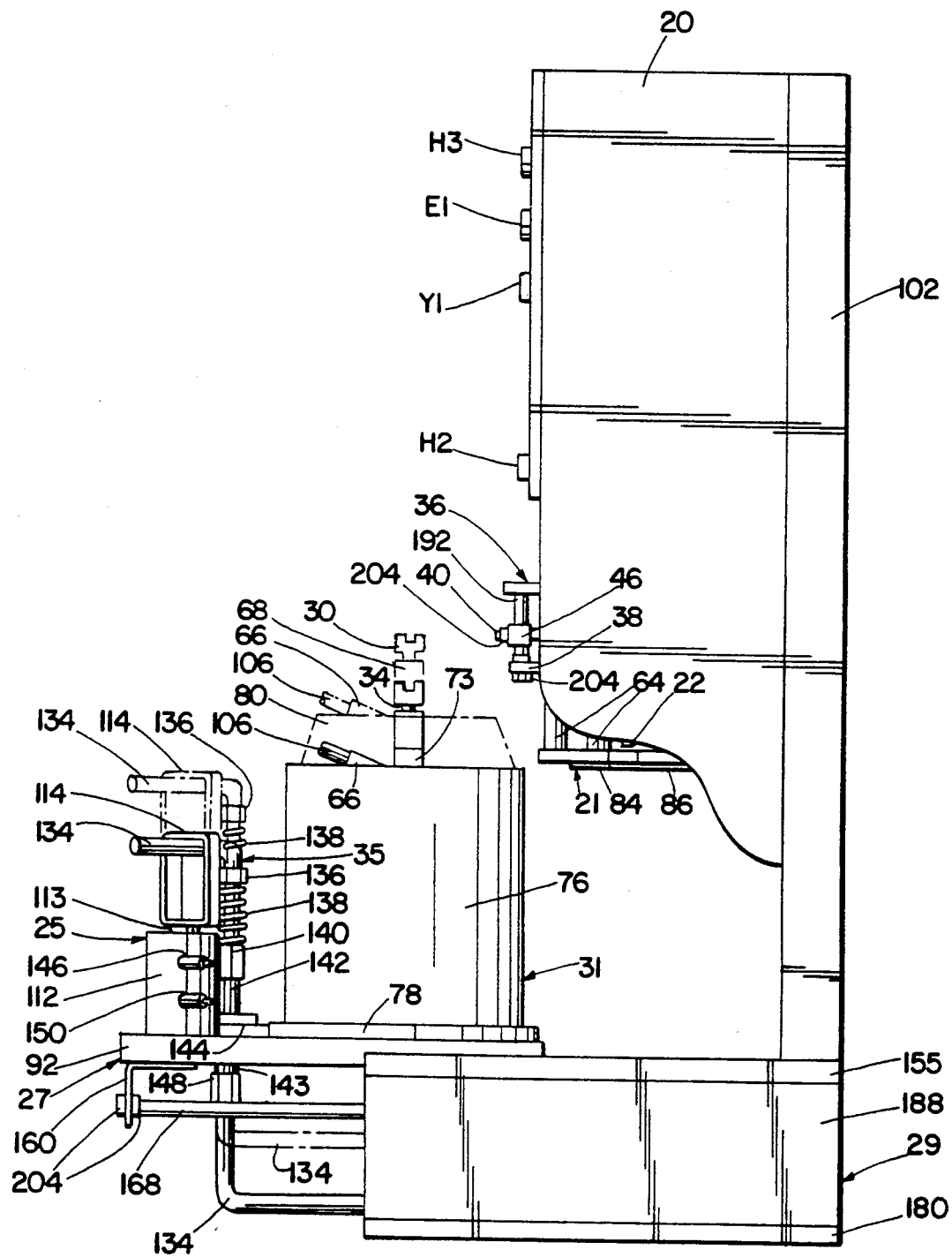
FIG. 3B is an elevational view of the right side of the invention showing the apparatus in the out-down position, with the phantoms showing the apparatus in the load-unload position.

FIG. 3B, in the phantom view, illustrates the upper horizontal portion of pressure-transfer bar 134, at the top of free-play unit 114, when said carriage assemblage is in the load-unload position (cf. FIG. 16).

Lid flange 82 is a circular portion of lid 70 attached on the top of said lid 70. The inside diameter of said lid flange 82 is less than the diameter of said lid 70, and the outside diameter of said lid flange 82 is greater than the diameter of said lid 70 (cf. FIGS. 5 and 10).

Lid apron flange 80 is used in conjunction with vessel apron flange 90 to direct used dirty and clean washing liquid obliquely outward and downward, away from mixing vessel 88 and from the interior of mixer cylinder 104. The two said apron flanges 80 and 90 are close but not touching when vacuum, suitable for vacuum mixing, is applied to said mixing vessel 88. Allowance should be made for wear of O-ring 96 when spacing said apron flanges 80 and 90 (cf. FIGS. 5).

Lid apron flange 80 fits tightly around lid flange 82 circumferentially, near the top, touching wing flanges 72 and 73, and extends obliquely outward and downward. The uppermost portion of said lid apron flange 80 is even with the horizontal plane of the top of surface of said lid flange 82. Said lid apron flange 80 is perforated with many small holes, placed close together, going around said lid apron flange 80, near the top. A material that bonds with said lid flange 82 is applied underneath to the junction of said lid flange 82 and lid apron flange 80, filling said holes, securing said lid apron flange 80, and sealing said junction.

Alternatively, one skilled in the art could make a removable and replaceable lid apron flange 80 by making the upper inside diameter smaller and making a slight groove in the upper outside surface near the top of said lid flange 82, then forcing said lid apron flange 80 into said groove. One can apply a seal or a sealant into said groove beforehand or to said junction after the attachment. Alternatively, one could form said lid 70, said lid flange 82 and said lid apron flange 80 together, or said lid flange 82 and said lid apron flange 80 together, then attach said lid flange 82 to said lid 70. One skilled in the art could choose another method for said attachment by which the same purpose could be accomplished.

Vessel apron flange 90 has a circular shape. The inward, top periphery of said vessel apron flange 90 encircles and is near the top outside corner of mixing vessel 88 and is fixedly attached to said mixing vessel 88. One uses a bonding material to bond said vessel apron flange 90 to said mixing vessel 88. such said materials are commercially available. Said vessel apron flange 90 extends obliquely outward and downward, and is used in conjunction with lid apron flange 80 to direct used washing liquid against channel base 98, against the interior wall of container 76, and away from the interior of mixer cylinder 104. said vessel apron flange 90 and lid apron flange 80 are part of the washing liquid disposal means.

Alternatively, one skilled in the art could make a vessel apron flange to be removable and replaceable as explained for lid apron flange 80 or one could form said vessel apron flange 90 with mixing vessel 88, or choose another method of said attachment.

Cylinder apron flange 94, in its entirety, encircles mixer cylinder 104. The top inward periphery of said cylinder apron flange 94 fits tightly around said mixer cylinder 104 (cf. FIGS. 5 and 14). said cylinder apron flange 94 is used to prevent upwardly forced washing liquid from entering mixer cylinder 104 at the location above the surface of the upper portion of channel base 98. Said location is the only place that said prevention is needed. Said cylinder apron flange 94 is slippable under force, removable and replaceable. One skilled in the art could make an attachment for said mixer cylinder 104 to accomplish the same purpose but said cylinder apron flange 94 is preferable and probably cheaper to manufacture and to attach to said mixer cylinder 104. Alternatively, one could make said cylinder apron flange 94 to be removable and replaceable as stated for said lid apron flange 80.

Six recessed vessel surfaces 198 (there could be more or less, but six are preferable) are obliquely slanted upward in the bottom of mixing vessel 88, are spaced evenly, and are formed to be suitable in size and in radial location to receive the end of no-spin pin 120 (cf. FIGS. 12 and 13). said no-spin pin 120 extends from above the top surface of discoid vessel support 130 to the bottom surface of discoid pressure plate 126. Resilient and retractable no-spin spring 122 fits loosely around, and pushes said no-spin pin 120 upward. Said recessed vessel surface 198 forces the end of said no-spin pin 120 to retract to the bottom surface of said mixing vessel 88 while said lid 70 is rotating said mixing vessel 88 during the alignment-guiding of said lid 70 to said lid hold 84. Each said recessed vessel surface 198 fits into a circular pattern and the two sides of each are arcuate, to be compatible with said pattern. One skilled in the art could form said recessed vessel surface 198 with a wider base, and disregard the curvature of said sides.

One end of each said recessed vessel surface 198 is formed perpendicular to the bottom surface of said mixing vessel 88. Said no-spin pin 120 holds on to said perpendicular end of said recess and prevents the potential rotation of said mixing vessel 88 while paddle 32 is rotating in the materials being mixed, and while rotating in said washing liquid.

An air compressor supplies filtered and regulated air pressure to the present invention by utilizing a flexible tube connected at each end by a connector to said present invention and to said air compressor, respectively. Said tube and said connectors are compatible, and are made to be connected or disconnected easily and quickly from said present invention or from said air compressor. Said tube and said connectors are available commercially where solenoid valves are purchased. Alternatively, one could make said connection rigid to a rigid air pressure supply pipe.

A flexible hose capable of withstanding suitable water pressure connects to said present invention at one end and to a water supply pipe at the other end. Said flexible hose has screw-on connectors at each end. Said connection, from said present invention to said water pressure, is like a connection made from a household clothes washer to water pressure. Other methods of making said connection, well known in the art, may be used, such as utilizing quick connectors, rigid fitting and piping and the like.

To begin the mixing cycle, one turns switch Y1 on to connect electrical supply L1 to the automatic vacuum mixer-washer apparatus of the present invention (cf. FIGS. 1 and 18B). The current flows through fuse F1
a) through switch A10 to switch H1, to the n.o. contacts of relay R1, and to switches H2 and H3.
b) through switch A1 to the n.o. contacts of relay R2.
c) to switch A2.
d) through switch A3 to the n.o. contacts of relay R5.
e) to the n.o. contacts of relays R8, R10 and a second set of n.o. contacts of relay R1.
f) through the n.c. contacts of relays R8 and R4 to switch A5, through switch A4 to n.o. contacts of relay R14, and to the n.o. contacts of relays R3 and R5, and to a second set of n.o. contacts of relay R14.

One then presses switch H1 to activate relay R1. This said preparatory action precedes starting a mixing cycle (when switch H2 is pressed), that utilizes vacuum while mixing, when a vacuum reserve cylinder is utilized. Switch A10 maintains the activation of said relay R1 through the n.o. contacts of relay R1. The current flows through the n.o. contacts of relay R1 and through the n.c. contacts of relay R10 to activate solenoid valve S1, enabling pressurized air to flow through a vacuum transducer pump, thereby creating vacuum in said vacuum reserve cylinder, a vacuum gauge and tubing 106 leading to solenoid valve s5.

Said vacuum reserve cylinder has a larger inside diameter than the rest of the tubing system, but is part of said tubing system and is referred to in total as tubing 106. Vacuum transducer pumps and vacuum reserve cylinders that have various capacities are available commercially. One chooses a vacuum transducer pump and vacuum reserve cylinder having sufficient capacity to create the optimum vacuum for the materials being mixing and for the size and strength of mixing vessel 88. Alternatively, one could substitute an electrically-powered vacuum pump for the vacuum transducer pump and solenoid valve S1.

A unit comprising in combination a mixing vessel, paddle, paddle shaft, conduit, bearing, bearing with vacuum seal, housing, lid, lid flange, O-ring and connector is available commercially. One may use said paddle, paddle shaft, bearing and bearing housing with vacuum seal, O-ring and connector without modification. Preferably, said connector may be modified to facilitate connection to socket pin 28 in socket 26 (see connector 30, illustrated in FIGS. 5, 7 and 8). Also, one may modify said mixing vessel, conduit, lid and lid flange for use in the vacuum mixer-washer apparatus of the present invention. Alternatively, one may manufacture mixing vessel 88, conduit 66, lid 70 and lid flange 82 for use in said vacuum mixer-washer apparatus (cf. FIGS. 5 and 10).

A mixing unit, as used in, and which is part of the present invention, comprises the following parts and characteristics in combination:

a. mixing vessel 88, comprises the following parts and characteristics in combination:
(1) a circumferential surface suitable for rotation for one revolution, in a direction counter to the direction, in which driving motor M2 rotates, and can easily slide axially within cylinder 104 (cf. FIG. 14) with no binding or wobbling (cf. FIGS. 5, 12 and 14),
(2) recessed vessel surface 198 (cf. FIGS. 12 and 13),
(3) vessel apron flange 90, attached to said mixing vessel 88 (cf. FIG. 5), b. lid 70, with which the following parts are combined or united, and each said part constituting a portion thereof, is hereby listed:
(1) lid flange 82
(2) O-ring 96
(3) lid apron flange 80
(4) left wing flange 72
(5) right wing flange 73
(6) paddle 32
(7) paddle shaft 34
(8) bearing and bearing housing with seal 68
(9) connector 30
(10) conduit 66
(11) tubing 106

Figure 11:
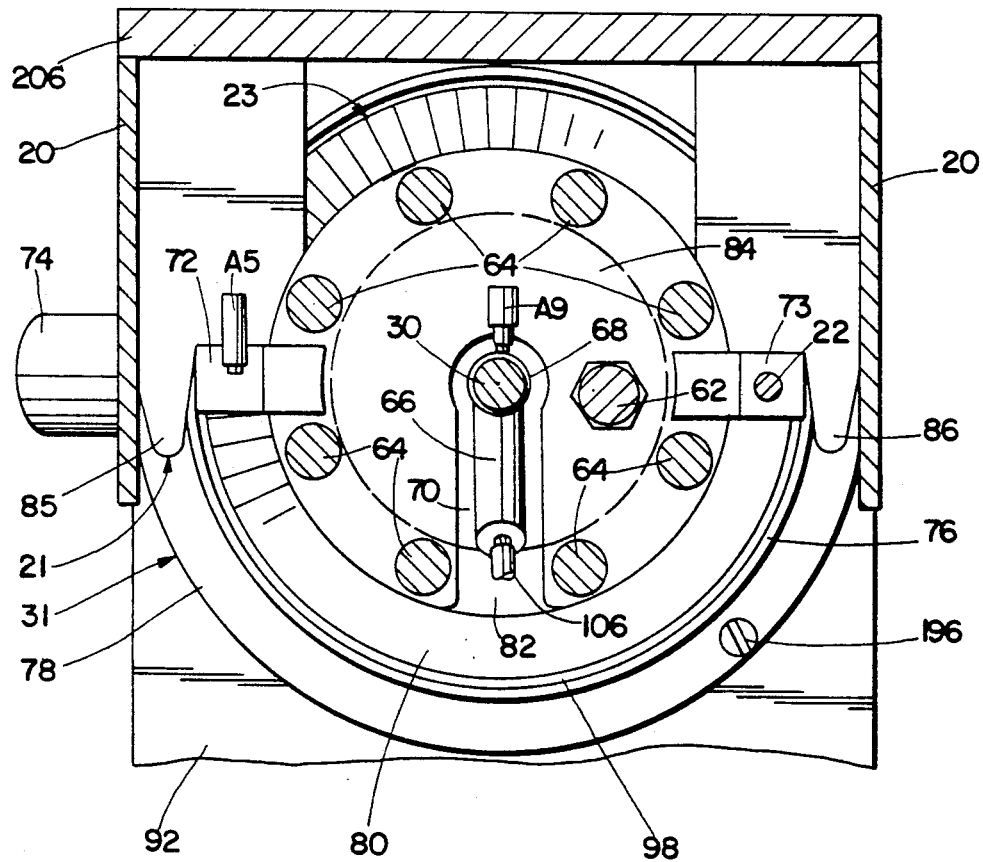
FIG. 11 is a sectional view as seen from line 11—11 in FIG. 2.

One then places the ingredients suitable for vacuum mixing in mixing vessel 88, and places said mixing vessel 88 on discoid vessel support 130 in mixer cylinder 104 and places lid 70 on top of said mixing vessel 88 such that left wing flange 72 is closer to left guide stop 85 than right wing flange 73 is to right guide stop 86 (see FIGS. 11 and 3B). Lid 70 fits loosely on the top of mixing vessel 88, with the bottom of said lid 70 extending partially into the top of said mixing vessel 88, thereby letting lid 70 or mixing vessel 88 turn counterclockwise, while lid 70 is moving into position beneath lid-hold 84.

Mixing vessel 88 and paddle 32 may assume any configuration desired. However, the outer diameter of mixing vessel 88 and the inner diameter of mixer cylinder 104 should be such that said mixing vessel 88 and the inner diameter of mixer cylinder 104 should be such that said mixing vessel 88 can easily rotate, counter to the direction in which said driving motor M2 rotates, and can easily slide axially within said mixer cylinder 104 without binding or wobbling.

Figure 14:
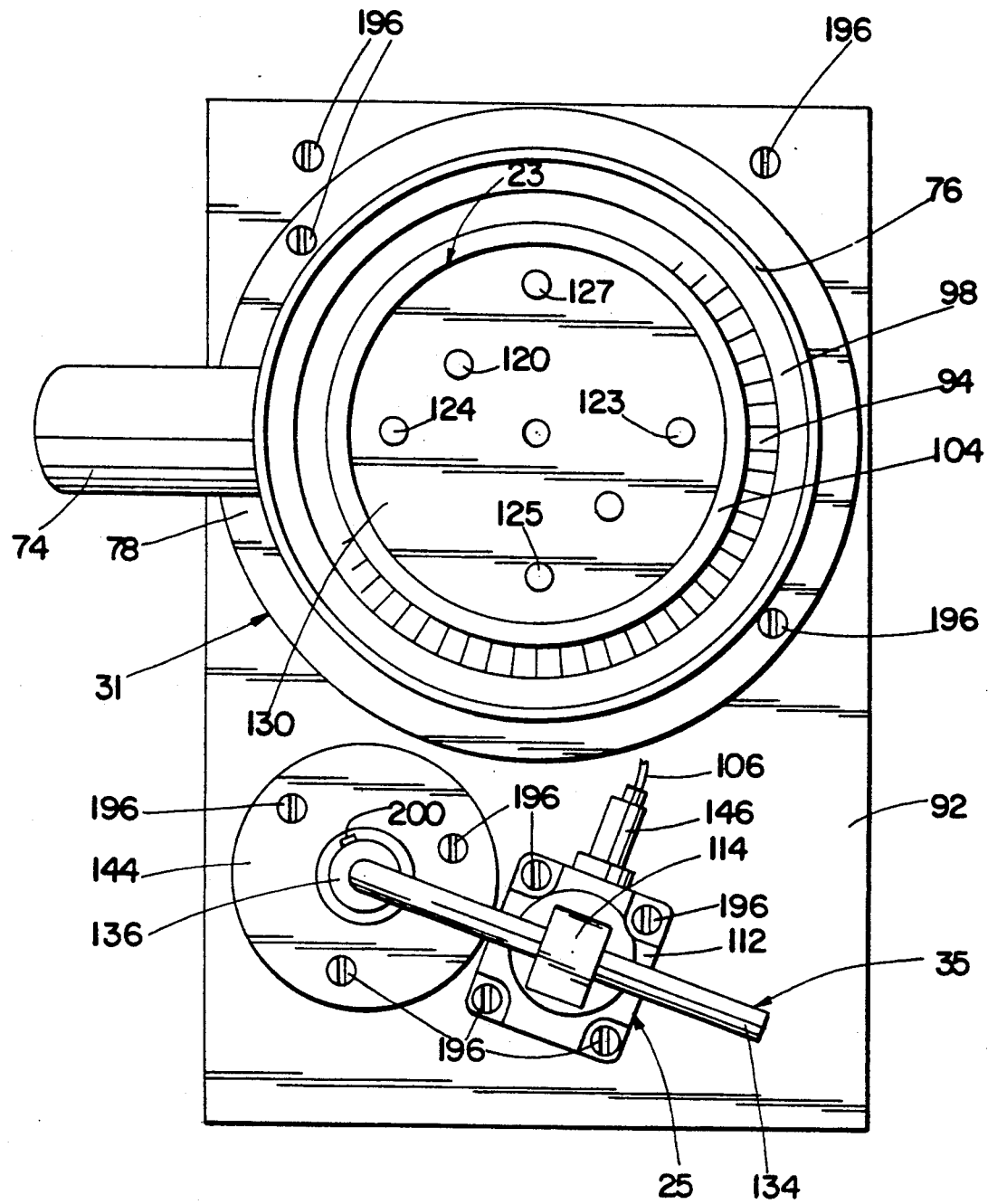
FIG. 14 is a top plan view, as seen from line 14—14 in FIG. 2, of mixer-washer assembly 23, vertical assembly 25, container assembly 31, and pressure-transfer assembly 35, with lid 70 and mixing vessel 88 removed.

FIG. 13 illustrates no-spin pin 120 and no-spin spring 122 assembled between discoid vessel support 130 and discoid pressure plate 126, with the top of said no-spin pin 120 located against the uppermost part of a recessed vessel surface 198 located in the bottom of mixing vessel 88 (cf. FIG. 12). Alternatively, a separate plate could be made with appropriate recessed vessel surfaces 198 and then attached permanently and concentrically to the bottom of mixing vessel 88. No-spin pin 120 can escape from recessed vessel surface 198 during the alignment of lid 70 beneath lid-hold 84 at which time mixing vessel 88 can rotate counterclockwise, along with lid 70 (cf. FIG. 11). During the mixing and washing operations, lid-hold 84 holds lid 70 from rotating clockwise as viewed from the top. During the washing operation, no-spin pin 120 holds mixing vessel 88 so that it cannot rotate when said mixing vessel 88 is forced downward slightly by the pressure of water, air or other washing liquid, which provides a narrow opening between mixing vessel 88 and lid 70 for liquid to pass, carrying suspended residue particles (cf. FIG. 5). No-spin pin 120 holds mixing vessel 88 from rotating in the direction of driving motor M2 rotation, when at a time, said mixing vessel 88 would be inclined to rotate, notably during the washing operation (cf. FIGS. 12 and 13).

shoulder pins 123, 124, 125 and 127 hold discoid pressure plate 126 and discoid vessel support 130 parallel to each other, providing sufficient space for no-spin pin 120 and to attach the top of pull-push bar 116 to discoid pressure plate 126 using compression pins 128 and 129 (cf. FIGS. 5 and 14).

One presses switch H2, thereby initiating the flow of current through relays R2 and R3 (cf. FIG. 18A). Switch A1 maintains the activation of said relays R2 and R3 through the n.o. contacts of relay R2. At this time, current flows through the n.o. contacts of activated relay R3, thereby activating solenoid valve S2. Said activated solenoid valve S2 activates up-down rod 113 of up-down cylinder 112 to move pressure-transfer bar 134, mixer-washer assembly 23 and activator-deactivator 132 down (cf. FIGS. 1 and 2), utilizing the total possible travel of up-down rod 113 of up-down cylinder 112 (cf. also FIGS. 15 and 16). During said downward movement, spring stop 136 compresses bar spring 138 against the top of top bearing 140, and discoid pressure plate 126 compresses push spring 110 against discoid pressure plate 118 (cf. FIG. 5).

As activator-deactivator 132 nears the end of its downward movement, plate 178 touches the lever of switch A2 (cf. FIGS. 15, 16 and 17), thereby initiating flow of current flow of current through said switch A2 to (cf. FIGS. 18A and 16):

a) binary digital timer, thereby starting a delay period
b) relay 5
c) solenoid valve S3
d) through the n.c. contacts of relay R11 to switches A6 and A8 to the n.o. contacts of relay R6, through n.c. contacts of switch A7 to a second set of n.o. contacts of relay R6, to two sets of n.o. contacts of relay R7, and to relay R4.

Any delay timer that accomplishes the same purpose may be used instead of said binary digital timer.

Activated relay R4 opens the n.c. contacts of said relay R4, thereby preventing, during the delay period, the flow of current that would otherwise come through the n.c. contacts of said relay R4 from the n.c. contacts of relay R8, whereby said flow of current remains prevented by said relay R8 until cam timer motor M1 stops.

A delay period is required to prevent premature activation of solenoid valves S2 and S6, which otherwise would abort the remainder of the mixing or washing operation, and return mixing vessel 88 and lid 70 to the load-unload position. The delay period makes it possible to connect mixing vessel 88 and lid 70 to lid-hold 84 and maintain said connection during the starting of either the mixing or washing operation. One selects the duration of the delay period so that it ends after cam timer motor M1 starts and before either the mixing or washing operation ends.

Since activated relay R4 prevents the flow of current to the contacts of n.o. switch A5, relay R14 cannot activate, consequently solenoid valve S2 cannot activate through the n.o. contacts of relay R14 and up-down cylinder 112 cannot activate. Activated relay R4 also prevents current flow through a second set of n.o. contacts of activated relay R5, thereby preventing activation of solenoid valve S6 which controls the action of lid-push cylinder 62. It is important that activated relay R4 prevents the flow of current through the closed contacts of n.o. switch A5 until cam timer motor M1 starts, at which time relay R8 activates whereby said flow of current remains prevented by said relay R8 until driving motor M2 stops. Said driving motor M2 is controlled by said relay R8.

Switch A3 (n.c.) maintains the activation of said relay R5, the binary digital timer, and solenoid valve S3 (cf. FIG. 18A). Said activated solenoid valve S3 activates in-out rod 168 of in-out cylinder 164, utilizing the total possible travel of said in-out rod 168, to start the inward movement of the carriage assemblage (see page 9, lines 17 through 22; also see FIGS. 3B, 14, 15 and 16).

Figure 10:
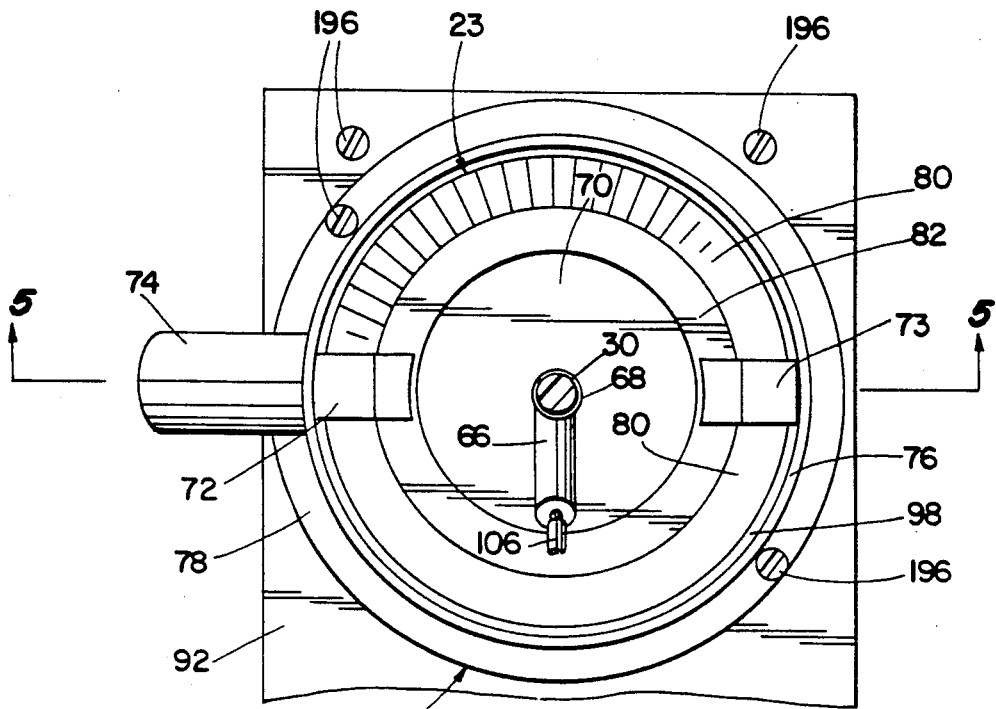
FIG. 10 is a top plan view of lid 70 covering mixing vessel 88 on container assembly 31 and carriage 92.

During this inward movement, the inner edge on the upper level of left wing flange 72 (cf. FIG. 5) contacts the outer arcuate edge of the left side of lid-hold 84 (cf. FIG. 11), thereby aligning partially with said lid-hold 84. Then the upper levels of left wing flange 72 and right wing flange 73 move against left guide-stop 85 and right guide-stop 86, respectively, thereby completing the alignment of lid 70 and mixing vessel 88 beneath lid-hold 84. Said wing flanges 72 and 73 are fixedly attached to lid flange 82 and are shaped as illustrated in FIGS. 5, 3B and 10. One skilled in the art could form said wing flanges 72 and 73 with lid 70 and said lid flange 82. Lid hold 84 (cf. FIG. 1) and guide stops 85 and 86 (cf. FIGS. 11 and 1) passively guide said wing flanges 72 and 73 as mixing vessel 88 and said lid 70 move and stop in alignment with, and beneath said lid hold 84, thereby aligning said wing flanges 72 and 73, said lid 70, and also aligning the center of connector 30, with the center of socket 26.

Near the end of the inward movement, bumper guide 184 prevents plate 178 from touching switch A3 (cf. FIG. 16). Alternatively, one can make bumper guides 182 and 184 longer and make 90 degree bends horizontally near the ends of said guides 182 and 184 so that the horizontal portions of said bumper guides 182 and 184 can make better contact with plate 178 at the appropriate times. Then deactivator 108 (cf. FIGS. 2, 15 and 16) deactivates switch A1, relays R2 and R3, and solenoid valve S2 (cf. FIG. 18A). When solenoid valve S2 deactivates, up-down rod 113 of up-down cylinder 112 moves upward, utilizing the total possible travel of said up-down rod 113. Simultaneously, push spring 110 and bar spring 138 expand, thereby moving pressure-transfer bar 134, activator-deactivator 132 (cf. FIG. 2) and mixer-washer assembly 23 upward (cf. FIG. 5).

The primary resilient and active support for said mixing vessel 88 and said lid 70 with tubing attached, and the rest of the total, previously described mixing unit, is said push spring 110. Said push spring 110 pushes the rest of the support for said mixing vessel 88 and said lid 70 upward, which includes discoid pressure plate 126, shoulder pins 123, 124, 125 and 127, and discoid vessel support 130. Said push spring 110 also pushes upward connector 30, no-spin pin 120, no-spin spring 122, compression pins 128 and 129, and also pulls pull-push bar 116 upward. When required said pull-push bar 116 pulls said discoid pressure plate 126 downward, thereby compressing said push spring 110.

Push spring 110, assembled on pull-push bar 116, between discoid pressure plate 126 and discoid pressure plate 118, pushes against discoid pressure plate 118 to effect upward movement of mixing vessel 88, and contents therein, until lid 70 moves against the bottom of lid-hold 84 and connector 30 attaches to socket pin 28 (cf. FIGS. 2, 5 and 11). Pull-push bar 116 passes through an aperture in discoid pressure plate 126 to which said pull-push bar 116 is fastened by compression pins 128 and 129, then passes through an aperture in discoid pressure plate 118 and through an aperture in carriage 92 (cf. FIG. 5). Discoid pressure plate 118 rests on an inward, circular projection of flange 78 (cf. FIG. 5).

To assemble pressure-transfer assembly 35, one screws the top end of bottom bearing 148 on to the bottom end of bottom pipe 143, the top end of bottom pipe 143 into the bottom of flange 144, the top of flange 144 on to the bottom end of top pipe 142, the top end of top pipe 142 into the bottom end of top bearing 140; one then passes pressure-transfer bar 134, either before or after bending said pressure-transfer bar 134 at a first time, through the aforesaid assembled parts and through bar spring 138 and spring stop 136 in proper order; after which one bends said pressure-transfer bar 134 a second time (cf. FIG. 2). Flange 144 attaches firmly to carriage 92, as FIG. 14 illustrates.

Figure 15:
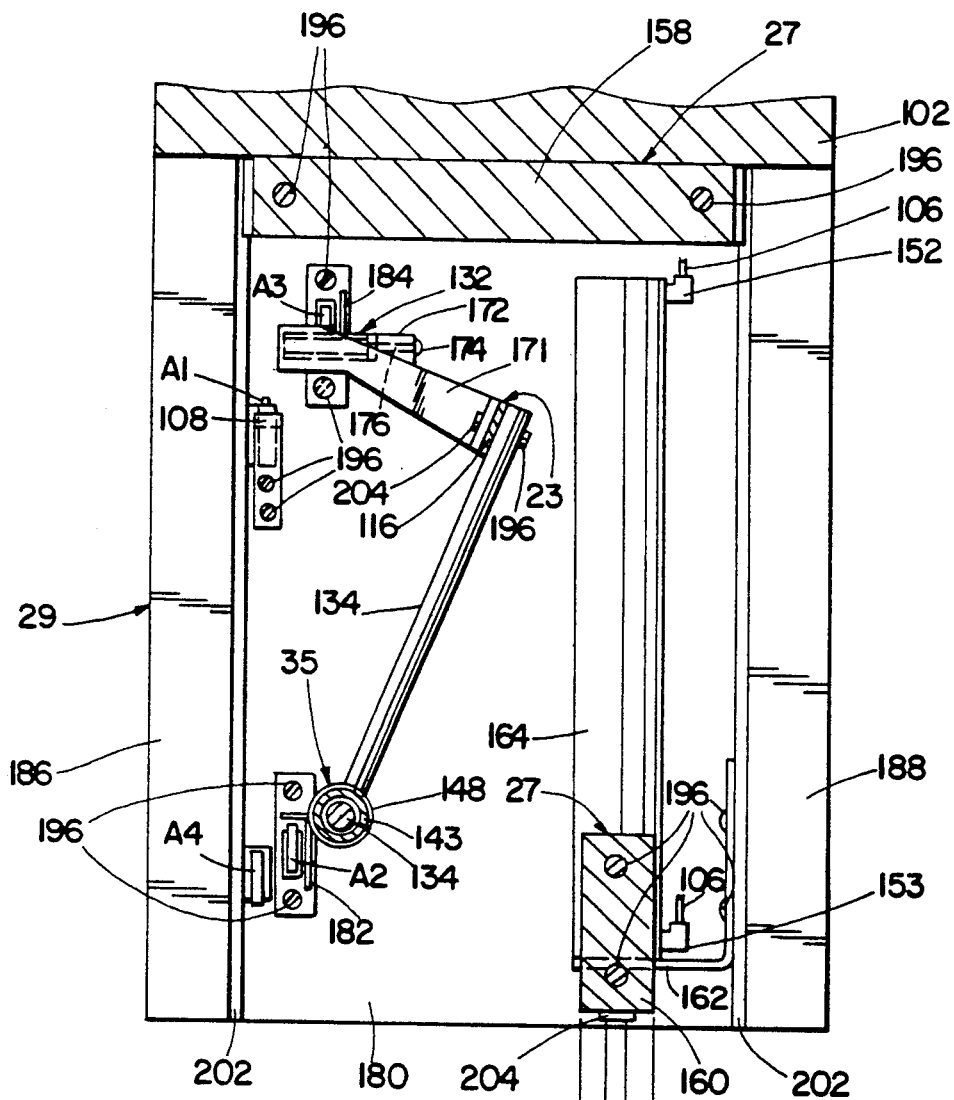
FIG. 15 is a top sectional view, as seen from line 15—15 in FIG. 2.
Figure 17:
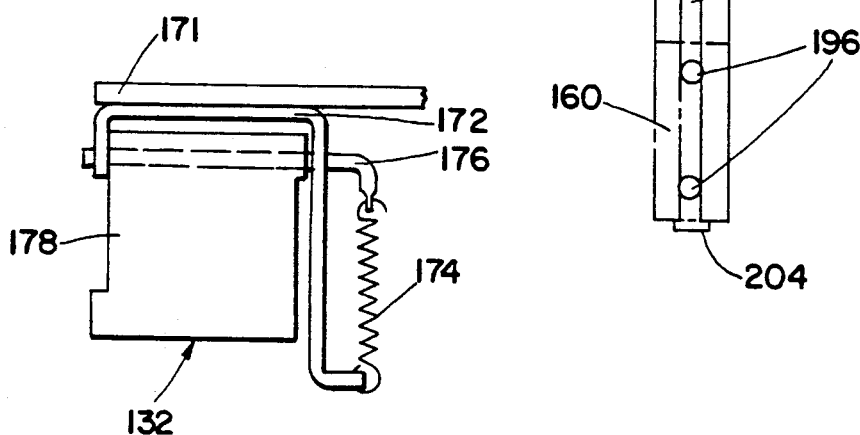
FIG. 17 is a front elevational view of activator-deactivator 132.

Pull-push bar 116 attaches to the end of the lower horizontal portion of pressure-transfer bar 134 in such manner as to allow pivotal movement, thereby avoiding undue stress at said attachment (cf. FIGS. 2 and 15). The strength of bar spring 138 is sufficient to lift the weight of pressure-transfer bar 134 and spring stop 136 (cf. FIG. 2).

Left wing flange 72 and right wing flange 73 move upward into the provided locations of lid-hold 84, while against left guide stop 85 and right guide stop 86 respectively, thereby holding lid 70 firmly in position. Left wing flange 72 and right wing flange 73 keep lid 70 from rotating while the discoid lowest portion of lid-hold 84 prevents radial movement of said lid 70 during mixing and during washing. As right wing flange 73 moves upward toward its stop position, said right wing flange 73 pushes spin pin 22 and protuberance 48 attached thereto, upward thereby activating switch A6, which in turn, activates relay R6, which in turn, activates solenoid valve S4. Switch A7 maintains the activation of said relay R6 until spin deactivator 58 deactivates n.c. contacts of said switch A7 (cf. FIGS. 2 and 9). Protuberance 48 is annular with a gradual outward slope from the surface of spin pin 22 to the outermost extent of said protuberance 48, and then with a gradual inward slope back to the surface of said spin pin 22. Protuberance 48 extends from the surface of spin pin 22 sufficiently so that it can activate the lever of switch A6. One places protuberance 48 on spin pin 22 such that said protuberance 48 activates switch A6 at the time when the top end of connector 30 is near to, but not touching, socket pin 28 (cf. FIGS. 5, 6, 7 and 8).

Connector 30 attaches to paddle shaft 34 at the top. Paddle 32 attaches to said paddle shaft 34 on the other end (cf. FIG. 5). FIGS. 6, 7 and 8 illustrate connector 30 in a bottom view, a side view, and a second side view showing said connector 30 rotated 90 degrees from that shown in FIG. 7, respectively. FIG. 8 illustrates a side view of the two prongs of connector 30. Each prong is beveled on the inner surface so as to make a slot that is wider at the top than at the bottom to facilitate entry of the two prongs of connector 30 into the areas along side of socket pin 28 in socket 26 (cf. FIG. 5). Again, referring to FIG. 8, one sees that each prong, on the outer surface near the top, is rounded to facilitate entry of connector 30 into the opening of socket 26. FIG. 7 shows how each prong is rounded at the top, thereby facilitating entry of each prong of connector 30 into the areas along side of socket pin 28 in socket 26.

FIG. 8 illustrates a bifurcated connector, however, one skilled in the art could make a connector with one prong or more than two prongs and a suitable receiving socket to serve the same purpose. FIG. 7 illustrates how each prong has an arcuate recess at each side of said figure (see also FIG. 8). One skilled in the art could make connector 30 without arcuate recesses in said connector 30 (cf. FIGS. 7 and 8). However, said arcuate recesses are preferred since they produce a positive hold on socket pin 28 during operation. Connector 30 attaches to paddle shaft 34 by any suitable means, such as threads, shrink fitting, or the like (cf. FIG. 5).

Said activated solenoid valve S4 activates spin cylinder 42, thereby moving spin rod 40, arm 46, and socket spinner assembly 36 in an outward direction so that spin strip 38 can rotate socket 26 slowly to facilitate union with connector 30 (cf. FIGS. 3A, 5 and 9). Said spin rod 40 slides through stationarily-mounted spin bearing 44 which prevents lateral motion of said spin rod 40 (cf. FIG. 9). When socket-spinner assembly 36 reaches the end of its outward movement, spin deactivator 58 deactivates switch A7, relay R6, and solenoid valve S4, thereby reversing the direction of travel of spin rod 40, arm 46 and socket-spinner assembly 36, to effectuate inward movement to the stationary position (cf. FIGS. 2 and 9). Spin strip 38, during its inward travel, maintains contact with socket 26, rotating it in the same direction as driving motor M2 turns. Bumper 60, made from rubber or other resilient material, reduces noise and shock when socket-spinner assembly 36 moves into stationary position (cf. FIG. 9). Arcuate recessed surface 41 in spin strip 38 permits socket 26 to spin freely during the mixing or washing operations (cf. FIG. 9). Socket-spinner assembly 36 fits into its provided space without excessive vertical or lateral movement.

Upward pressure from previously retracted push spring 110, effectuates the upward movement of said connector 30 to permit said connector 30 to connect to said socket pin 28, within said socket 26.

Alternatively, one could rotate manually, said socket 26, to connect said connector 30 to said socket pin 28 by pulling and pushing pull pin 192, or one could rotate said socket 26 by hand for said connection (cf. FIGS. 3A and 3B).

When left wing flange 72 reaches its upward stop position, it closes the contacts of switch A5 but no current flows through said switch A5 during the delay period or while switch A10 activates relay R8 because activated relay R8 opens the circuit leading to said switch A5 (cf. FIG. 18A). Spinner-hold 37 aids in holding socket-spinner assembly 36 in its designated upright position by fitting loosely against recessed spinner surface 39.

Also, as right wing flange 73 moves further upward into its stop position, it pushes spin pin 22 and protuberance 48 attached thereto further upward, thereby deactivating switch A6. It is important that switch A6 is deactivated so that switch A7 can effectuate the inward movement of socket-spinner assembly 36 at the appropriate time. At a later time, when spin pin 22 and protuberance 48 move down to protuberance stop 190 (cf. FIGS. 2 and 9), protuberance 48 cannot activate switch A6 even though it closes the contacts of said A6 temporarily, because the binary digital timer, after expiration of the said delay period, activates relay R11, thereby opening the n.c. contacts of said relay R11, thus preventing flow of current to said switch A6 (cf. FIGS. 2 and 18A). Also, arm 46 connects to strip 50 of timer-activator 100, as shown in FIGS. 1 and 9. Timer-activator 100 activates relay R7 so that current flows through the closed contacts of n.o. switch A9 (cf. FIG. 11) and cam timer motor M1 which is fitted with four cams that operate switches A10, A11, A12 and A13. The cam timer and motor M1 are available commercially. Other types of controllers such as delay timers or electronic controllers can be used for timing and/or signalling the solenoid valves. Said switch A9 (cf. FIG. 11) is ensconced to prevent inadvertent starting of cam timer motor M1 and is used to permit positive connection of connector 30 to socket pin 28 to occur before permitting said cam timer motor M1 to start. The top rounded periphery of the housing, included in bearing and bearing housing with seal 68, operates the roller and lever of said switch A9. One skilled in the art could eliminate said switch A9 to reduce manufacturing cost.

Figure 4:
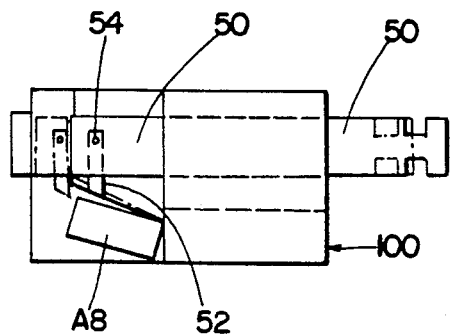
FIG. 4 is an elevational view of the left side of timer-activator 100 showing activation of switch; the phantom shows deactivation of said switch.

FIG. 4 illustrates timer-activator 100 as viewed from the left side of the automatic vacuum mixer-washer apparatus comprising the present invention (see also FIG. 9). Timer-activator 100 serves first, to allow trigger 52 to pivot on trigger pin 54 to bypass switch A8 as strip 50 moves outwardly (to the right); second, to activate said switch A8 as said strip 50 moves inwardly (to the left); third, when trigger 52 clears said switch A8, said switch A8 deactivates as strip 50 reaches the end of the inward movement (cf. FIG. 4).

Said strip 50 (cf. FIG. 4) attached to arm 46, moves simultaneously with socket-spinner assembly 36 (cf. FIGS. 1 and 9). When socket-spinner assembly 36 and strip 50 approach the end of their inward travel, trigger 52 activates switch A8 which in turn, initiates activation of relay R7 (cf. FIGS. 4 and 9). Switch A3 (n.c.) maintains said activation of relay R7 through the n.o. contacts of relay R5, the n.c. contacts of relay R11, and the n.o. contacts of relay R7 (c.f. FIG. 18A). Said activated relay R7 sends current through the n.o. contacts of switch A9 because bearing and bearing housing with seal 68 closed the contacts of said switch A9 when lid 70 and mixing vessel 88 moved into position beneath and against lid-hold 84 (cf. FIGS. 11 and 18A). Said current, after passing through switch A9, goes through fuse F2 to cam timer motor M1 during the delay period of the binary digital timer (cf. FIG. 18A). During the said delay period, said cam timer motor M1 turns the cam for switch A10 to lift the roller on the lever of said switch A10 out of its notched recess, thereby activating switch A10 to send current to said cam timer motor M1 so that switch A10 can operate and control said cam timer motor M1 after the said delay period expires.

Simultaneously, switch A11 sends current to activate relay R9 which in turn, activates relay R10 and solenoid valve S5 (cf. FIG. 18A). Said activated solenoid valve S5 opens the vacuum reserve, thereby aiding lid 70 to seal to mixing vessel 88 and creating a vacuum in said mixing vessel 88. The vacuum reserve is useful because it permits the rapid application of vacuum to mixing vessel 88. Said activated relay R10 now takes over operation and control of solenoid valve S1 (cf. FIG. 18A). Previously, switch H1 activated relay R1 to pass current through n.c. contacts of relay R10 to operate solenoid valve S1.

Simultaneously, current flows through switch A10 to relay R8, thereby starting driving motor M2 and preventing the flow of current through n.c. contacts of relay R8 to solenoid valves S2 and S6. At this point, driving motor M2 mixes the ingredients under vacuum in mixing vessel 88, using paddle 32. Driving motor M2 (cf. FIG. 2) is fixedly attached to support 102. Cam timer motor M1 operates said cam timer, which times the operation of said driving motor M2. One skilled in the art could build said apparatus, wherein said driving motor M2 could be movable and guided to connect said socket 26 and socket pin 28 with connector 30. Alternatively, said driving motor M2 could be attached to a wall of other supporting structure.

One chooses the mixing speed and duration to achieve uniform mixing of the particular ingredients used and/or to remove entrapped air or other gases from the mixture. Mixing speed could range between about 0.1 to about 10,000 revolutions per minute (rpm). Speeds in the lower end of said range would be useful for mixing viscous, fragile, radioactive, or biological materials, such as microorganisms growing in nutrient solutions. Speeds in the upper end of said range would be used for materials that need to be mixed quickly and uniformly. For example, a preferred range for mixing dental stone for models or for mixing plaster for making castings or molds for the casting of metal or other substances requiring dimensional accuracy is about 500 to about 5,000 rpm, with a range between 1,000 and about 3,500 rpm most preferred. The preferred duration of mixing for materials most generally used for preparing models is about one second to about 60 seconds. For mixing dental lab stone, a more preferred duration is about four seconds to about 16 seconds. For mixing regular setting lab plaster, a more preferred duration is about two to about 14 seconds. The vacuum mixer-washer apparatus, in either the automatic or semi-automatic embodiment, is very useful in mixing lab stone, investment or plaster because it mixes very rapidly and produces a smooth and reproducible blend consistently in mix after mix. The smoothly blended, gas-free material produces models, molds or castings that are highly accurate. The recommended duration of washing after mixing and removing dental stone is approximately 10 to 50 seconds.

Alternatively, the mixing and/or washing cycles can be extended to many seconds, minutes, hours, weeks or months. For example, the mixer-washer apparatus of the present invention could be made to mix biological materials, such as microorganisms, while they are growing in nutrient solution. At the end of the timed growth phase, one could expel the mixture from the mixing vessel and then automatically wash said mixing vessel. Such a mixer-washer is very useful in producing toxic microorganisms or chemicals or for mixing cement or other materials continuously until needed, and then washing said mixing vessel after the cement or other materials have been emptied from said mixing vessel. The duration of the washing cycle is selected to ensure efficient cleansing.

The said delay period now expires and the said binary digital timer activates relay R11, thereby opening the n.c. contacts of said relay R11 and deactivating relay R4. When relay R4 deactivates, the n.c. contacts of relay R4 close (cf. FIG. 18A).

Switch A10 shuts off the vacuum mixing operation when cam timer motor M1 has turned the cam, thereby lowering the roller of the lever of said switch A10 into a notched recess in said cam. Simultaneously, switch A10 deactivates relay R8, thereby releasing current through the n.c. contacts of said relay R8, the n.c. contacts of relay R4, and through the n.o. contacts of still-activated relay R5 to activate solenoid valve S6 (cf. FIG. 18A). Said activated solenoid valve S6 activates lid push rod 194 in lid push cylinder 62, thereby separating lid 70 from lid-hold 84, thus pulling said connector 30 from socket 26 (also see FIG. 18B). When said lid 70 separates, wing flange 72 moves away from switch A5, thereby opening the contacts of said switch A5.

Simultaneously, while the current is still flowing through the n.c. contacts of relays R8 and R4 and the closed contacts of n.o. switch A5, relay R14 activates, allowing current to flow through the n.c. contacts of relay R3 to activate solenoid valve S2 (cf. FIGS. 18A), thereby activating up-down rod 113 of up-down cylinder 112 and starting downward movement of mixer-washer assembly 23, pressure-transfer bar 134, and activator-deactivator 132 (cf. FIGS. 2 and 5). When plate 178 reaches the end of downward travel, said plate 178 deactivates switch A3 (cf. FIG. 16), thereby deactivating relay R5 (cf. FIG. 18A). Said deactivated relay R5 shuts off the current to the binary digital timer, thereby resetting said binary digital timer for use in a later operation. Simultaneously, said deactivated relay R5 deactivates solenoid valve S6, thereby reversing the travel of lid push rod 194 so that it moves back into lid-push cylinder 62 (cf. FIG. 19). Simultaneously, said deactivated relay R5 deactivates solenoid valve S3 (cf. FIG. 18A), thereby starting outward movement of in-out rod 168 of in-out cylinder 164 (cf. FIGS. 3B and 15) which effectuates the outward movement of the carriage assemblage (cf. page 9, lines 17 through 22; also see FIGS. 3B, 14 and 15), utilizing the total possible travel of said in-out rod 168 of in-out cylinder 164 (cf. FIGS. 3B and 15). FIG. 16 illustrates plate 178 as it bumps into bumper guide 182, thereby preventing said plate 178 from contacting the lever of switch A2. At the end of the outward travel, deactivator 108 deactivates switch A4, which in turn, deactivates relay R14, thereby deactivating solenoid valve S2, which then raises up-down rod 113 out of up-down cylinder 112, utilizing the total possible travel of said up-down rod 113 of said up-down cylinder 112 (cf. FIGS. 15 and 16). As said up-down rod 113 moves upward, mixer-washer assembly 23, pressure transfer bar 134, and activator-deactivator 132 move up to the load-unload position, thereby ending the automatic vacuum mixing cycle. One lifts mixing vessel 88 and attached lid 70 out of mixer cylinder 104, touches switch H3 momentarily, thereby activating solenoid valve S8 to release the vacuum in said mixing vessel 88, and removes the contents thereof. However, some residue remains behind on paddle 32, on the inner surfaces of lid 70 and said mixing vessel 88, necessitating thorough washing. In an embodiment which utilizes air pressure through solenoid valve S8, one skilled in the art could additionally install solenoid valve S9 to facilitate the use of atmospheric air to eliminate vacuum within said mixing vessel 88, instead of using air pressure for said purpose as stated above.

To start the automatic washing cycle, one places mixing vessel 88 into mixer cylinder 104, positions lid 70 and pushes switch H2 momentarily, whereupon, said lid 70 and said mixing vessel 88 move beneath and against lid-hold 84 as described previously for the mixing cycle (cf. FIGS. 3A and 3B). One does not need to press switch H1 because no vacuum is applied during the washing cycle. At this time, switch A10 sends current through switches A11 and A12, thereby activating relay R12 (cf. FIG. 18A). Current then flows through the n.o. contacts of relay R12, through the n.c. contacts of relays R9 and R13 to solenoid valve S7, thereby enabling water or other washing liquid to flow through tubing 106 and conduit 66 into mixing vessel 88. Although under normal operations tubing 106 is never disconnected from conduit 66, said tubing 106 is connected removably and tightly to said conduit 66 so that liquid or air pressure will not separate said tubing 106 from said conduit 66 during the washing operation (cf. FIGS. 10 and 11).

Simultaneously, switch A10 activates relay R8, thereby sending current to driving motor M2 (cf. FIG. 18A) and spinning paddle 32 in mixing vessel 88 during the time when water or other washing liquid is flowing, obtaining sufficient agitation to clean thoroughly said paddle 32, O-ring 96, area adjacent to said O-ring 96, the bottom surfaces of lid 70, inner surfaces of mixing vessel 88, and lower portion of paddle shaft 34.

Water or other washing liquid continues to flow into mixing vessel 88, pressure builds up until said mixing vessel 88 separates slightly from lid 70. Said separation occurs because water or other washing liquid exerts greater downward pressure on said mixing vessel 88 than push spring 110 and bar spring 138 exert upward. At this time, water or other washing liquid flows over the top of mixing vessel 88, carrying suspended residue particles with it, between lid apron flange 80 and vessel apron flange 90, around the outside of mixer cylinder 104, inside of container 76, over the top surface of channel base 98, and out through flow pipe 74 (cf. FIGS. 5 and 3B). Cylinder apron flange 94 prevents water or other washing liquid from entering inside mixer cylinder 104 (cf. FIG. 5).

As illustrated in FIG. 5, channel base 98, formed by pouring a measured amount of plaster-water mixture between the inner wall of container 76 and the outer wall of mixer cylinder 104 and vibrating said container 76 while holding at an angle necessary to align the top surface of channel base 98 with the inner bottom of flow pipe 74, and about ¼-inch below the bottom of cylinder apron flange 94. Said cylinder apron flange 94 encircles mixer cylinder 104 and is adjacent to the underside of vessel apron flange 90 when mixing vessel 88 is in its downward stop position. Said channel base 98 directs waste wash liquid from mixing vessel 88 and out through flow pipe 74. The upper surface of channel base 98 may be sealed by painting with a suitable sealer, thereby forming a smooth surface impervious to liquid. One skilled in the art could make a similar device by other methods, such as welding assembled parts, plastic molding, or the like.

Switch A12 now switches relay R12 and solenoid valve S7 off (cf. FIG. 18A), thereby ending the water flow. Simultaneously, switch A12 sends current through switch A13, activating relay R13 and sending current through the n.o. contacts of relay R13 to solenoid valve S8, thereby starting flow of air through tubing 106 and conduit 66 into mixing vessel 88. The air enters said mixing vessel 88 while paddle 32 is spinning rapidly, thereby purging most of the clean water or other washing liquid, from said mixing vessel 88 and tubing 106, by exerting sufficient pressure to separate mixing vessel 88 from lid 70.

Switch A13 now deactivates relay R13, thereby deactivating solenoid valve S8. Switch A10 stops current flow to cam timer motor M1 and to relay R8 (cf. FIG. 18A), thereby stopping driving motor M2 and returning lid 70 and mixing vessel 88 to the load-unload position, as described previously at the end of the mixing cycle.

FIG. 18B illustrates a schematic diagram of a preferred embodiment of the automatic vacuum mixer-washer apparatus of the present invention. In this embodiment, resistor Z1 restricts the flow of current for a time period of less than approximately one second to driving motor M2 so that motor shaft 24 and socket 26 attached thereto, turn slowly, thereby facilitating connection of connector 30 to socket pin 28 in said socket 26 (cf. FIGS. 2 and 5). Using this preferred method, one can eliminate from the automatic vacuum mixer-washer apparatus comprising the present invention the following:

| Part | Figures |
|---|---|
| Socket-spinner assembly 36 | 1, 9 |
| Timer-activator 100 | 4, 9 |
| Switches A7, A8 and A9 | 9, 11 |
| Solenoid valve S4 | 18A |
| Spin cylinder 42 | 9 |
| Relay R7 | 18A |
| Spin bearing 44 | 9 |
| Spinner-hold 37 | 2 |
| Fittings 156 and 170 | 9 |
| Tubing 106 (between spin cylinder 42 and solenoid valve S4) | 9 |

Said resistor Z1 is used for automatic connection of connector 30 to socket 26 (cf. FIGS. 5, 6, 7, 8, 18B and 18D). Said resistor Z1 permits motor shaft 24 and socket 26 to rotate slowly for less than 180 degrees, thereby aligning socket pin 28 with the furcations of connector 30, subsequently said connector 30 moves rapidly into said socket 26. Said movement of said connector 30 initiates automatic start of cam timer motor M1 by releasing wing flange 73 to push spin pin 22 upward, causing switch A6 to activate relay R6. Each one of several resistors will effectuate said automatic connection (i.e., 2 ohm through 5 ohm–25 watts each; 2 ohm–60 watts; and 3 ohm–100 watts; 3 ohm–100 watts is preferable). One skilled in the art may choose a different resistor to use. A commercially available light dimmer can be used instead of said resistor Z1.

Alternatively, one could use an automatic connector to facilitate connection of connector 30 to socket pin 28 in socket 26. Using this alternative method, one can further eliminate from the automatic vacuum mixer-washer apparatus of the present invention the following:

| Part | Figure |
|---|---|
| Spin pin 22 | 2 |
| Protuberance 48 | 2 |
| Guide 56 | 2 |
| Protuberance stop 190 | 2 |
| Resister Z1 | 18B |

One skilled in the art could then reposition switch A6, attaching said switch A6 to right guide stop 86 such that wing flange 73 can activate and deactivate said switch A6 as lid 70 moves against lid-hold 84.

In one semi-automatic embodiment (cf. FIG. 18D) of said mixer-washer apparatus wherein no gaseous pressure is to be utilized, for movement of carriage 92, one uses downward hand pressure on the top horizontal portion of pressure-transfer bar 134 to retract push spring 110. One holds down, while pushing forward, said pressure-transfer bar 134 to obtain and maintain sufficient clearance for said lid 70 during alignment of said lid 70 with said lid hold 84, while going beneath said lid hold 84, to mix-wash position. After said alignment, one releases said pressure-transfer bar 134, thus permitting said push spring 110 to push said lid 70 against said lid hold 84, to move connector 30 upward for connection with socket pin 28, within socket 26, and to effectuate the starting of cam timer motor M1. Subsequently, driving motor M2 slowly rotates said socket 26 for less than 180 degrees and for less than one second to effectuate or to ensure connection of said connector 30 to socket pin 28. Simultaneously, while connector 30 slides upward within socket 26, connecting with socket pin 28, said lid 70 moves upward, against said lid hold 84. One reverses above said procedure to move said mixing vessel 88 and said lid 70 from mix-wash position to load-unload position by first applying downward finger pressure on lid flange 82 for quick release of said lid 70 from said lid hold 84, while pressing on, and moving said pressure-transfer bar 134 downward, after which, the rest of said reverse procedure is continued. In said embodiment, each of two operations start and perform automatically, namely: (1) mixing operation and (2) washing operation; however, one skilled in the art could eliminate said automatic start by installing an electric switch for manual activation, by which to start each said operation.

One skilled in the art could make lid 70 heavy and/or form holes in said lid hold 84 to help in releasing said lid 70 from said lid hold 84, thereby eliminating said downward finger pressure.

This semi-automatic operation is easily accomplished by an operator, by first, pushing switch H1 momentarily to start the vacuum; second, placing into mixer cylinder 104, mixing vessel 88 with materials suitable for vacuum mixing within said mixing vessel 88, with lid 70 on top of said mixing vessel 88 and with tubing attached to said lid 70; third, pushing down on pressure-transfer bar 134 until it reaches the end of its downward movement; fourth, pushing it toward the back of said vacuum mixer-washer apparatus until carriage 92 stops; and fifth, guiding said pressure-transfer bar 134 upward until lid 70 touches lid-hold 84 and right wing flange 73 pushes spin-pin 22 upward, thereby activating switch A6 which starts cam timer motor M1. During this operation, lid 70 is automatically aligned with lid hold 84 (cf. FIGS. 3B and 18D). Vacuum mixing is then performed automatically. When mixing stops, the operator first applies downward finger pressure on lid flange 82, while pushing pressure transfer bar 134 down until it reaches the end of downward travel; second, pulls it to the front, until the back of lid 70 clears the front of lid hold 84 (if desired, a carriage stop is easy to make or obtain and is simple to install); third, guides said pressure-transfer bar 134 upward until lid 70 and mixing vessel 88 reach the load-unload position. When pressurized air tubing is not attached to solenoid valve S8 for air pressure to enter tubing 106, one activates switch H3 to release atmospheric air through said solenoid valve S8, thus through said tubing 106, to eliminate vacuum within said mixing vessel 88. After pressing switch H3, then emptying said mixing vessel 88, the operator repeats the same starting procedure for the washing cycle except that switch H1 is not pressed because no vacuum is needed during the washing cycle. After washing, one activates switch H4, utilizing solenoid valve S8, to drain tubing 106.

The difference between the semi-automatic and automatic embodiments is that an operator moves lid 70 and mixing vessel 88 from the load-unload position to the mix-wash position and back to the load-unload position manually during the semi-automatic operation whereas said movement is performed automatically in the automatic vacuum mixer-washer apparatus. The advantage of said semi-automatic vacuum mixer-washer apparatus is a much lower manufacturing cost than for one having the automatic features. To reduce manufacturing cost still more, one could build an embodiment wherein one would eliminate pressure-transfer bar 134, whereupon an operator would guide lid 70 and mixing vessel 88 directly into the mix-wash and load-unload positions manually.

In said embodiment of said mixer-washer apparatus, wherein, said apparatus does not have said pressure transfer bar 134 to be utilized, one pushes wing flanges 72 and 73 downward, with the thumbs, thus moving lid 70 and mixing vessel 88 downward, compressing push spring 110, until pull-push bar 116 touches base 180. While holding said wing flanges 72 and 73 down, one has their hands on container 76, and thus manually, moves said container 76 inward, to beneath lid hold 84, and later, outward, from beneath said lid hold 84. Alternatively, one could shorten said pull-push bar 116 and attach a bracket to the underside of carriage 92, to stop said pull-push bar 116 which would stop said downward movement. One skilled in the art could make a different stop for said downward movement and eliminate said pull-push bar 116.

Figure 18E:
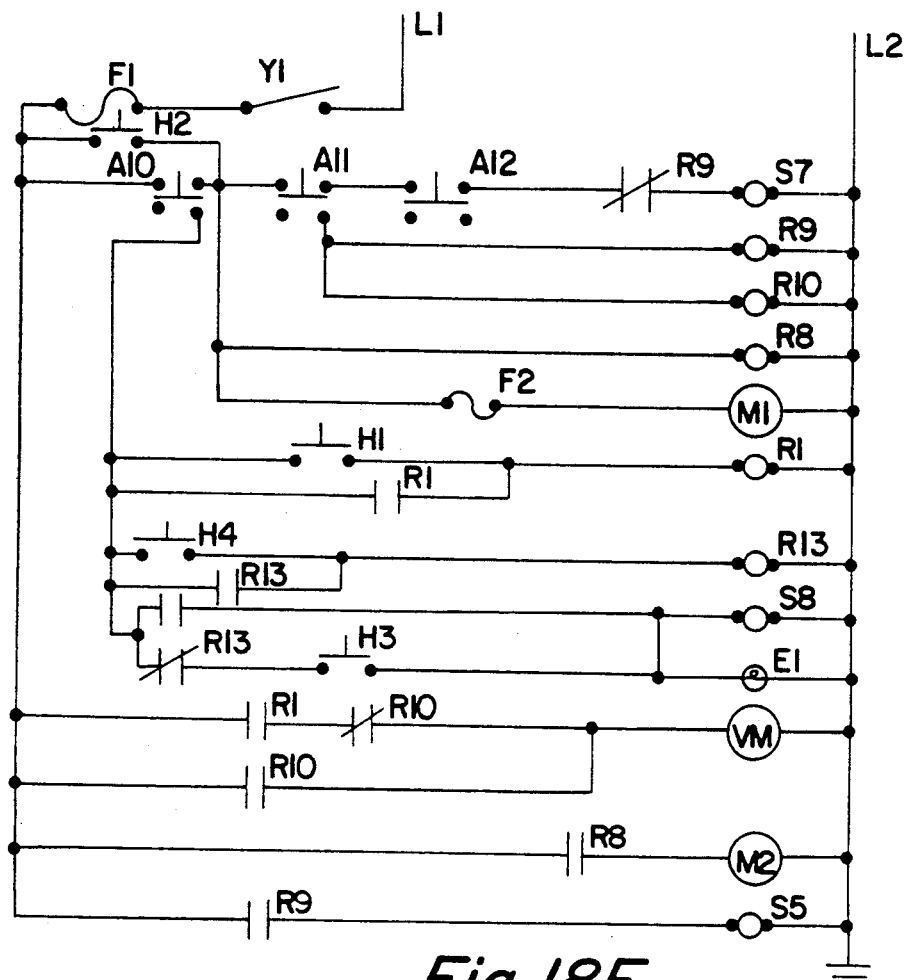
FIG. 18E is a schematic wiring diagram of a semi-automatic embodiment of the vacuum mixer-washer apparatus, similar to that of FIG. 18C except that FIG. 18E includes a means for applying vacuum to tubing 106 before mixing is started (see page 34, lines 30 through 42).

FIG. 18E illustrates an embodiment of said semi-automatic vacuum mixer-washer apparatus which requires no air pressure for operation. To operate this embodiment of said vacuum-mixer washer apparatus, an operator first, presses switch H1 to start vacuum motor VM; second, moves lid 70 and mixing vessel 88 to the mix-wash position as described previously; third, presses switch H2 to start cam timer motor M1. Vacuum mixing then proceeds automatically. After manually moving lid 70 and mixing vessel 88 to the load-unload position and then pressing switch H3 to release the vacuum, the operator empties mixing vessel 88, and repeats the same procedure for starting the washing cycle except that switch H1 is not pressed because no vacuum is needed during the washing cycle. Solenoid valve S5 also serves to isolate the water line from the vacuum source. Solenoid valve S7, when activated by switch A12, opens to permit water under pressure to enter mixing vessel 88. After the washing cycle is completed, the operator presses switch H4 to allow water to drain from tubing 106, which is connected to solenoid valves S5, S7 and S8. To lower manufacturing cost, pressure-transfer assembly 35 may be withdrawn from FIG. 18E embodiment or from the embodiment shown in schematic diagram FIG. 18C.

Figure 18C:
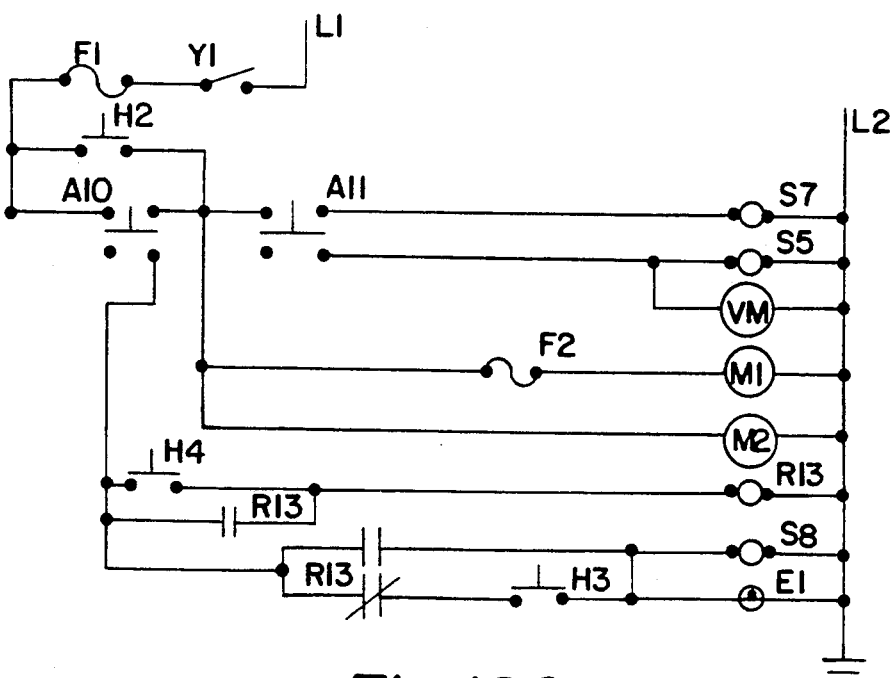
FIG. 18C is a schematic wiring diagram of a semi-automatic embodiment of the vacuum mixer-washer apparatus that has no vacuum reserve and requires no air pressure for operation.

FIG. 18C illustrates another embodiment of said semi-automatic vacuum mixer-washer apparatus which requires no air pressure and less components for operation, thereby reducing manufacturing cost. To operate this vacuum mixer-washer apparatus, one uses the same procedure described for FIG. 18E except for pressing switch H1. Switch H1 has been eliminated. The vacuum starts when the mixing starts.

The embodiments of said semi-automatic vacuum mixer-washer apparatus, as described for FIGS. 18C and 18E, are made so that water can drain out of tubing 106 by gravity into mixing vessel 88 after the washing cycle. During the washing cycle, incoming water entering through solenoid valve S7 is in contact with solenoid valve S5 (the vacuum outlet) and solenoid valve S8 (the atmosphere inlet), therefore said solenoid valves S7, S5 and S8 are oriented for maximum drainage. Tubing 106 is slanted downwardly and forms a singular passage to conduit 66, which passes through lid 70 to mixing vessel 88 (cf. FIGS. 10 and 11).

One skilled in the art could use a commercially available air pump, with or without a commercially available air reserve cylinder to facilitate blowing air through tubing 106 at the end of the washing cycle, or instead, a vibrator could be used to vibrate said tubing 106.

After the washing cycle, one presses switch H4 to activate solenoid valve S8 to effectuate drainage of tubing 106. When said tubing 106 has drained sufficiently, one presses rocker switch Y1 to the off position, or, if operator is ready to start mixing again, said operator just presses switch H2 at the appropriate time.

An electrician skilled in the art can assemble and connect the necessary electrical parts of said vacuum mixer-washer apparatus. Likewise, an electrician skilled in the art could apply a portion of any of wiring schematics FIGS. 18A through 18E to suit the requirements of any embodiment of the present invention.

In these pages, the term "timing means" is intended to be synonymous with, and is referred to as "cam timer motor M1."

Figure 18D:
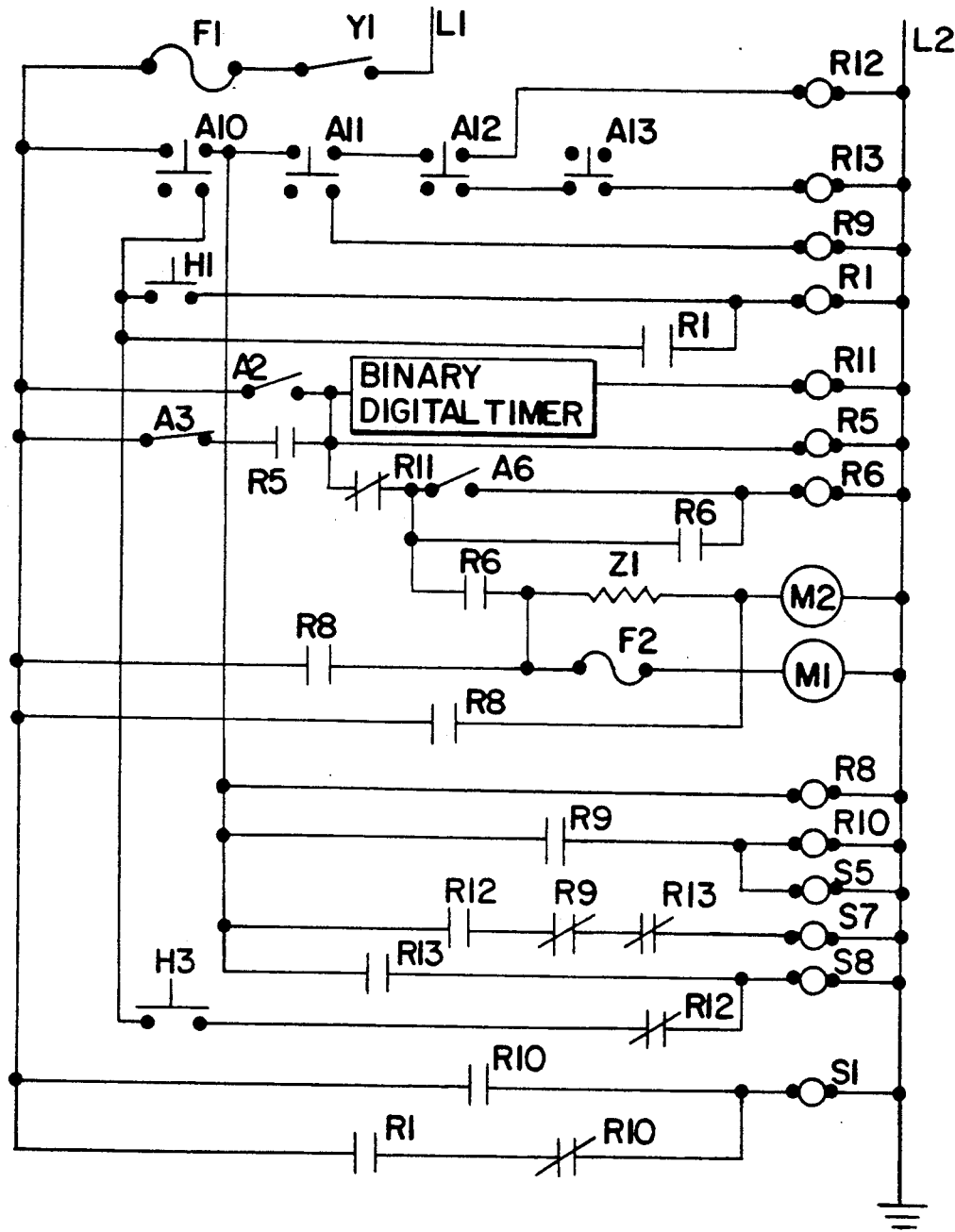
FIG. 18D is a schematic wiring diagram of a semi-automatic embodiment of the vacuum mixer-washer apparatus similar to the automatic vacuum mixer-washer apparatus described in FIG. 18B except that lid 70 and mixing vessel 88 must be moved into the mix-wash and load-unload positions manually.

In the schematic diagram of the embodiment illustrated in FIG. 18A, automatic start of the timing means, namely, cam timer motor M1, is accomplished as described on page 27, lines 26 through 41. In FIG. 18B, automatic start of said cam timer motor M1 is described on page 32, lines 14 through 24. In FIG. 18D, the start of said cam timer motor M1 is accomplished in the manner as described for FIG. 18B but is used only when manual use of pressure-transfer bar 134 is utilized in the mixing and/or washing operations.

In FIG. 18E, manual start of said cam timer motor M1 is required. In FIG. 18C, manual start of said cam timer motor M1 is required (see page 35, lines 5 through 10).

In another embodiment, one skilled in the art could build said embodiment wherein vacuum could be applied to the interior of mixing vessel 88 and to lid 70, either while in the load-unload position or before placing said mixing vessel 88 along with vacuum-held lid 70 into said load-unload position and either said action could be chosen by the operator at the appropriate time.

One embodiment of the vacuum mixer-washer apparatus of the present invention is that in which the driving means and lid-hold 84 move to attach to or separate from connector 30 and lid 70. Another embodiment of said vacuum mixer-washer apparatus is that in which the driving means, fastened to paddle shaft 34 and lid 70, moves to attach to or separate from mixing vessel 88. Another embodiment of said mixer-washer apparatus is one in which said driving means moves to attach to, or separate from mixing vessel 88 and in which paddle shaft 34 removably fastens to the rotating portion of driving motor M2. One provides means for providing resiliency to said driving motor M2 to permit said driving motor M2 to lift slightly during the washing operation when washing liquid or air pressure increases to permit escape of said washing liquid. Methods to enable said driving means to move, such as, by sliding or by using roller bearings, for example, are well known in the machinist trade and such device can be made easily by one skilled in the art.

I claim:

1. A mixer-washer apparatus comprising in combination:
   a. a base,
   b. driving means, including a driving motor,
   c. frame means,
   d. housing means,
   e. support means, including support for said driving motor,
   f. mixing means, including a mixing vessel, paddle, connector and lid with tubing attached, and capable of continuous or cyclic operation,
   g. means for holding said mixing vessel,
   h. means for holding said lid,
   i. means for connecting said mixing means to said driving means,
   j. means for connecting to, and utilizing washing liquid for washing,
   k. means for sealing said mixing vessel against leakage of air and/or liquid,
   l. means for preventing potential rotation of said mixing vessel during mixing and during washing,
   m. means for holding said mixing means in load-unload position, in mix-wash position, and during movement between the two said positions,
   n. means for moving said mixing means between said load-unload position and said mix-wash position,
   o. means for positioning said mixing means in said load-unload position, in said mix-wash position, and in any required intermediate temporary position,
   p. resilient supporting means, for said mixing means,
   q. means for retracting said resilient supporting means,
   r. means for releasing said resilient supporting means,
   s. alignment-guiding means for said lid, for alignment with said lid holding means, when guiding said mixing means to said mix-wash position,
   t. washing liquid disposal means,
   u. means for timing the duration of mixing operation, washing operation and operation of said driving motor,
   v. means for permitting partial rotation of said mixing vessel and said lid during said alignment-guiding of said lid,
   w. means for preventing radial movement of said mixing vessel,
   x. means for starting said timing means,
   y. means for supporting and guiding said mixing means between said load-unload position and said mix-wash position,
   z. means for separating said lid from said holding means,
   aa. conveyance means, for holding, supporting, carrying and guiding:
      (1) said mixing means, (2) said resilient supporting means, for said mixing means,
(3) said means for retracting said resilient supporting means,
(4) said washing liquid disposal means, for channeling washing liquid from said mixing vessel to a drain,
bb. support and guidance means, for said conveyance means,
cc. means for moving said conveyance means from load-unload position to mix-wash position and from mix-wash position to load-unload position,
dd. means for holding and supporting all parts, used in said apparatus, to form the total said apparatus.

2. The mixer-washer apparatus set forth in claim 1 wherein said driving means moves to connect to said mixing means and later to disconnect from said mixing means.

3. The mixer-washer apparatus set forth in claim 1 wherein an operator moves said mixing means manually to connect said mixing means to said driving means and later to disconnect said mixing means from said driving means.

4. The mixer-washer apparatus set forth in claim 1 wherein said apparatus also includes a vacuum means for vacuum mixing, timing for the application of said vacuum, and means for eliminating said vacuum after mixing.

5. The mixer-washer apparatus set forth in claim 1 wherein said apparatus also includes means for connecting to and utilizing gaseous pressure, and timing means for the application of said gaseous pressure.

6. The mixer-washer apparatus set forth in claim 1 wherein said apparatus incorporates two automatic cycles, namely: (1) mixing cycle, and (2) washing cycle, wherein said washing cycle also includes means to expel and dispose of washing liquid from said mixing vessel to a drain, and each said cycle begins and ends at a time when said conveyance means is in load-unload position, and each cycle starts by manually activating an electric switch.

7. The mixer-washer apparatus set forth in claim 1 wherein said driving means, said mixing means and said washing means are in essentially vertical position.

8. The mixer-washer apparatus set forth in claim 1 wherein said driving means, said mixing means, and said washing means are in a position between about 1 degree and about 90 degrees from vertical position.

9. The mixer-washer apparatus set forth in claim 1 wherein said mixer-washer apparatus comprises also, in combination, vacuum reserve means for rapidly sealing said lid to said mixing vessel and for quickly removing air and/or other gases from said mixing vessel and from the materials being mixed.

10. A mixer-washer apparatus comprising in combination:
a. a base,
b. support means,
c. housing means,
d. movable and guided driving means, including a driving motor,
e. guidance means for said driving means, comprising in combination:
  (1) a stationary guidance fixture attached to said support means,
  (2) a movable guidance fixture attached to said driving means,
f. means to move said driving means,
g. movable frame means attached to the nonrotatable portion of said driving motor,
h. lid, removably attached to said frame means,
i. paddle shaft, removably attached to the rotatable shaft of said driving motor,
j. mixing means,
k. mixing vessel,
l. means for holding said mixing vessel,
m. means for holding said mixing means,
n. means for connecting to and utilizing washing liquid under pressure for washing,
o. means for preventing potential rotation of said mixing vessel during mixing and washing,
p. means for sealing said mixing vessel against leakage of air and/or washing liquid,
q. means for moving and guiding said driving means to and from the mixing position and the washing position,
r. washing liquid disposal means,
s. means for sequentially timing the duration of mixing, and duration of washing,
t. means for starting said timing means,
u. resilient driving motor supporting means,
v. means for slowly rotating driving motor shaft, less than 180 degrees, for connecting said driving means to said mixing means,
w. means for holding and supporting all parts that are used in said apparatus to form the total said apparatus.

11. The mixer-washer apparatus set forth in claim 10 wherein said apparatus comprises also, in combination, vacuum means for vacuum mixing, means for timing the utilization of said vacuum means, and means for releasing air to the interior of said mixing vessel to eliminate said vacuum, trapped within said mixing vessel after mixing.

12. The mixer-washer apparatus set forth in claim 10 wherein said apparatus also includes means for connecting to and utilizing gaseous pressure and means for timing the application of said gaseous pressure.

13. A vacuum mixer-washer apparatus comprising in combination:
a. a base placed upon a supporting surface or attached to a wall or other supporting structure,
b. support means,
c. housing means,
d. frame means attached to and extending from said support means and/or said housing means, or attached to a wall or other supporting structure,
e. driving means, attached to said support means, or other supporting structure,
f. mixing means, including:
  (1) a mixing vessel, which is part of a mixing unit,
  (2) lid, with means for sealing to said mixing vessel,
  (3) mixing paddle, attached to a rotatable shaft, and extending through said lid, and capable of continuous or cyclic operation by said driving means,
g. means for holding said mixing vessel in required position before, during and after mixing operations and before, during and after washing operations,
h. means for holding said lid in required position before, during and after said mixing operations and before, during and after said washing operations,
i. means for connecting said mixing means to said driving means, j. vacuum means for removing air or other gases from the interior of said mixing vessel and from the materials being mixed,
k. means for moving and guiding said mixing means between the load-unload position and the mix-wash position,
l. means for positioning said mixing means in load-unload position and in mix-wash position,
m. means for washing the dirty surfaces of said lid, said mixing paddle, said rotatable shaft, said lid sealing means, area adjacent to said lid sealing means, and interior surfaces of said mixing vessel,
n. disposal means for channeling washing liquid from said mixing vessel to a drain,
o. means for timing:
  (1) said mixing means,
  (2) said driving means, during both said mixing and washing operations,
  (3) said vacuum means,
  (4) said washing means,
p. means for positioning said lid against said lid holding means,
q. means for separating said lid from said lid holding means,
r. means for starting said timing means,
s. alignment-guiding means, for said lid,
t. means for preventing potential rotation of said mixing vessel during both mixing and washing,
u. means for permitting potential rotation of said mixing vessel during said alignment-guiding of said lid,
v. means for releasing air to the interior of said mixing vessel and to said lid, to eliminate said vacuum, trapped within said mixing vessel,
w. resilient support means, for said mixing unit,
x. means for retracting said resilient support means,
y. means for releasing said resilient support means,
z. conveyance means, for holding, supporting, carrying and guiding:
  (1) said mixing unit,
  (2) said resilient support means, for said mixing unit,
  (3) said means for retracting said resilient support means,
  (4) said disposal means, for channeling washing liquid from said mixing vessel to a drain,
aa. support and guidance means, for said conveyance means,
bb. means for moving said conveyance means from load-unload position to mix-wash position and from mix-wash position to load-unload position,
cc. means for holding and supporting all parts that are used in said apparatus, to form the total said apparatus.

14. The vacuum mixer-washer apparatus set forth in claim 13 wherein said driving means moves to connect to, and also to disconnect from, said mixing means.

15. The vacuum mixer-washer apparatus set forth in claim 13 where one retracts said resilient support means manually, moves said conveyance means manually, then releases said resilient support means to connect said mixing means to said driving means and also to position said lid against said lid holding means, then reverses said procedure each time said timing means stops.

16. The vacuum mixer-wash apparatus set forth in claim 13 wherein said apparatus incorporates an automatic vacuum-mixing cycle and an automatic washing, washing liquid expelling and disposal cycle, and each said cycle begins and ends when said conveyance means is in said load-unload position and each said cycle begins by manually activating an electrical switch.

17. The vacuum mixer-washer apparatus set forth in claim 13 wherein said apparatus is in essentially vertical position.

18. The vacuum mixer-washer apparatus set forth in claim 13 wherein said apparatus is in a position ranging from about 1 degree to about 90 degrees from vertical position.

19. The vacuum mixer-washer apparatus set forth in claim 13 wherein vacuum is applied to the interior of said mixing vessel and to said lid before starting the mixing operation.

20. The vacuum mixer-washer apparatus set forth in claim 13 wherein air pressure applied to a vacuum transducer pump creates vacuum.

21. The vacuum mixer-washer apparatus set forth in claim 13 wherein said means for timing starts automatically.

22. The vacuum mixer-washer apparatus set forth in claim 13 wherein said vacuum means includes a vacuum reserve, thereby enabling rapid seal of said lid to said mixing vessel and to quickly remove air and/or other gases from said mixing vessel and from the materials being mixed.

23. The vacuum mixer-washer apparatus set forth in claim 13 wherein said apparatus also includes gaseous pressure means and timing means for using said gaseous pressure means.

24. A vacuum mixer-washer apparatus for mixing dental materials, preferably dental stone, comprising in combination:
a. a base placed upon a supporting surface or attached to a wall or other supporting structure,
b. frame means, attached to and extending from said base, or attached to a wall or other supporting structure,
c. housing means,
d. driving means,
e. support means, including support for a driving motor,
f. mixing means, including:
  (1) a mixing vessel, which is part of a mixing unit,
  (2) lid, with means for sealing said lid against passage of air or liquid around a rotatable shaft,
  (3) means for sealing lid to said mixing vessel, for holding vacuum,
  (4) means for channeling water and air through said lid,
  (5) tubing, attached to said means for channeling water and air through said lid,
  (6) mixing paddle, attached to said rotatable shaft, and said rotatable shaft extending through said lid, and capable of continuous or cyclic operation by said driving means, through an intermediate connector,
g. means for holding said mixing vessel in required position before, during and after mixing operations, and before, during and after washing operations,
h. means for holding said lid in required position before, during and after said mixing operations and before, during and after said washing operations,
i. means for positioning said lid against said lid holding means,
j. means for connecting said mixing means to said driving means, k. means for separating said lid from said lid holding means, and disconnecting said mixing means from said driving means,
l. means for expelling washing liquid from said mixing vessel,
m. vacuum means, for removing air and/or gases from within said mixing vessel and from the materials being mixed,
n. means for moving and guiding said mixing means between the load-unload position and the mix-wash position,
o. means for positioning said mixing means in load-unload position and in mix-wash position,
p. means for washing the dirty interior surfaces of said mixing vessel, and for washing the dirty surfaces of said lid, of said paddle, of said rotatable shaft, of lid sealing means, and the area around said lid sealing means,
q. disposal means, for channeling washing liquid from said mixing vessel to a drain,
r. means for timing:
  (1) said mixing operation,
  (2) operation of said driving motor during said mixing and washing operations,
  (3) the use and application of said vacuum,
  (4) said washing operation,
s. means for starting said timing means,
t. means for holding and applying reserve vacuum to the interior of said mixing vessel, to said lid and to said mixing means, to rapidly seal said lid to said mixing vessel and to quickly remove air and/or other gasses from said mixing vessel and from the materials being mixed,
u. means for eliminating vacuum trapped within said mixing vessel,
v. resilient support means, for said mixing means,
w. means for retracting said resilient support means, to permit and/or effectuate:
  (1) disconnection of said mixing means from said driving means,
  (2) separation of said lid from said lid holding means,
  (3) movement of said lid to provide sufficient clearance between said lid and said lid holding means for said lid to move beneath said lid holding means, before said positioning of said lid against said lid holding means, and after said separation of said lid from said lid holding means,
x. means for releasing said resilient support means, to permit connection of, and/or to connect said mixing means to, said driving means, and simultaneously to permit said positioning of, and/or to position, said lid against said lid holding means,
y. means for rotating the shaft of said driving motor sufficiently slow for less than 180 degrees to connect and/or ensure said connection of said mixing means to said driving means, which simultaneously positions and/or ensures said positioning of said lid against said lid holding means,
z. means for preventing potential rotation of said mixing vessel during mixing and during washing,
aa. means for permitting partial rotation of said mixing vessel during alignment-guiding of said lid,
bb. conveyance means, for holding, supporting, carrying and guiding:
  (1) said mixing means,
  (2) said resilient support means, for said mixing means,
  (3) said means for retracting said resilient support means,
  (4) said disposal means, for channeling washing liquid from said mixing vessel to a drain,
cc. support and guidance means, for said conveyance means,
dd. means for moving said conveyance means from load-unload position to mix-wash position and from mix-wash position to load-unload position,
ee. means for retracting said resilient support means for said mixing means and simultaneously separating said lid from said lid holding means,
ff. means for draining washing liquid from said tubing,
gg. means for holding and supporting all parts that are used in said apparatus to make the total said apparatus.

25. The vacuum mixer-washer apparatus set forth in claim 24 wherein said driving means moves to connect to, and also to disconnect from, said mixing means.

26. The vacuum mixer-wash apparatus set forth in claim 24 wherein one moves said mixing means manually to connect said mixing means to said driving means and to disconnect said mixing means from said driving means.

27. The vacuum mixer-washer apparatus set froth in claim 24 wherein said resilient support means moves automatically to connect said mixing means to said driving means and to permit disconnection of said mixing means from said driving means.

28. The vacuum mixer-washer apparatus set forth in claim 24 wherein said apparatus is in essentially vertical position.

29. The vacuum mixer-washer apparatus set forth in claim 24 wherein said apparatus is in a position ranging from about 1° to about 90° from vertical position.

30. The vacuum mixer-washer apparatus set forth in claim 24 wherein vacuum is applied to the interior of said mixing vessel, and to said lid and to said mixing means before starting the mixing operation.

31. The vacuum mixer-washer apparatus set forth in claim 24 wherein said driving means attaches to said support means.

32. The vacuum mixer-washer apparatus set forth in claim 24 wherein said means for starting said timing means functions automatically.

33. The vacuum mixer-washer apparatus set forth in claim 24 wherein air pressure, applied to a vacuum transducer pump, creates vacuum for vacuum mixing, and wherein the creation and application of said vacuum is automatically timed.

34. The vacuum mixer-washer apparatus set forth in claim 24 wherein means for connecting to, and utilizing air pressure is incorporated for:
  a. use in pneumatic cylinders (filtered, metered and regulated),
  b. expelling washing water from said mixing vessel and tubing (filtered, regulated and timed),
  c. eliminating vacuum, trapped within said mixing vessel (filtered and regulated).

35. The vacuum mixer-washer apparatus set forth in claim 24 wherein said conveyance means supports, holds and automatically moves, carries and guides the following between the load-unload position and the mix-wash position, namely:
  a. a mixing unit, with a connector and tubing attached to said mixing unit,
  b. resilient support means, for said mixing unit, c. means for retracting said resilient support means,
d. switching means, attached to said means for retracting said resilient support means, for operating stationary electric switches while said conveyance means is not moving,
e. switching means, attached to said conveyance means, for operating stationary electric switches while said conveyance means is moving,
f. washing liquid disposal means,
g. means for holding said mixing vessel and said lid in different appropriate positions when required,
h. means for positioning said lid against lid holding means,
i. part of means for starting said timing means,
j. means for holding conveyance means against conveyance support and guidance means, before, during and after movement between load-unload position and mix-wash position,
k. means for connecting to a rod of a pneumatic cylinder,
l. part of means for preventing potential rotation of said mixing vessel, formed into the exterior bottom surface of said mixing vessel,
m. part of means for permitting partial rotation of said mixing vessel, formed into same said surface,
n. part of means for preventing said potential rotation in the same rotational direction as a driving means and also permitting said partial rotation in the opposite direction, having resiliency and attached to said resilient support means,
o. alignment-guidance means, for said lid attached to a flange of said lid, which is part of said mixing unit.

36. The vacuum mixer-washer apparatus set forth in claim 24 wherein said apparatus has two automatic cycles, namely: (1) a vacuum mixing cycle, and (2) a combination washing, and washing liquid expelling-disposing cycle, and each said cycle begins and ends at a time when said conveyance means is in said load-unload position, and an operator starts each said cycle by manually activating an electrical switch.

37. The vacuum mixer-washer apparatus set forth in claim 24 wherein said apparatus comprises also in combination:
　a. means to move said driving means to connect to said mixing means before mixing, to disconnect from said mixing means after mixing, also to connect to said mixing means before washing, and to disconnect from said mixing means after washing,
　b. guidance means, comprising in combination:
　　(1) a movable guidance fixture attached to said driving means,
　　(2) stationary guidance fixture that guides said movable guidance fixture, with said stationary guidance fixture attached to said support means.

38. The vacuum mixer-washer apparatus set forth in claim 24 wherein said means for connecting said mixing means to said driving means, comprises in combination:
　a. a connector having two rounded prongs tapered away from the end of said prongs toward the inside of said prongs to facilitate connection of said connector to a socket pin and wherein said prongs taper away from the end toward the outside of said prongs to facilitate entry of said connector into a socket,
　b. a resistor installed in an alternate electrical circuit to said driving means, thereby restricting momentarily the flow of electrical current to said driving means, thereby starting said driving means slowly, and therefore facilitating and ensuring rapid connection of said mixing means to said driving means.

39. The vacuum mixer-washer apparatus set forth in claim 24 wherein said means for connecting said mixing means to said driving means comprises in combination:
　a. a connector having two rounded prongs tapered away from the end of said prongs toward the inside of said prongs to facilitate connection of said connector to a socket pin and wherein said prongs taper away from the end toward the outside of said prongs to facilitate entry of said connector into a socket,
　b. a socket spinner assembly to revolve said socket slowly to facilitate and ensure connecting said mixing means to said driving means.

40. The vacuum mixer-washer apparatus set forth in claim 24 wherein an electric motor creates vacuum for vacuum mixing.

41. A mixer-washer apparatus comprising in combination:
　a. a base,
　b. support means, including support for a driving motor,
　c. frame means,
　d. housing means,
　e. driving means, including said driving motor,
　f. mixing means, including:
　　(1) a mixing vessel,
　　(2) lid with means for sealing to said mixing vessel,
　　(3) tubing, attached to said lid,
　　(4) paddle, attached to a rotatable shaft, extended through a bearing housing, bearing, seal, and said lid, wherein said rotatable shaft is attachable to said driving means,
　g. resilient support means, for said mixing vessel,
　h. means for retracting said resilient support means,
　i. means for preventing potential rotation of said mixing vessel during the mixing operation and during the washing operation,
　j. alignment-guiding means for said lid,
　k. means for permitting a partial revolution of said mixing vessel and said lid, for, and during said alignment-guiding of said lid,
　l. means for applying vacuum to the interior of and holding said vacuum within said mixing vessel during the mixing operation,
　m. means for connecting to, and utilizing a supply of washing liquid under pressure, to wash the dirty interior surfaces of said mixing vessel, the dirty surfaces of said lid, of said paddle, of said rotatable shaft, of said means for sealing said lid, and of the area adjacent to said means for sealing said lid,
　n. means for timing:
　　(1) the application of vacuum,
　　(2) the duration of operation of said driving means,
　　(3) the duration of said mixing,
　　(4) the duration of said washing,
　　(5) the duration of vacuum use,
　o. means for disposing of dirty washing liquid,
　p. means for positioning and for retracting said means for mixing,
　q. means for connecting said rotatable paddle shaft to said driving means,
　r. means for draining unwanted washing liquid from said tubing,
　s. means for starting said timing means, t. means for supporting and guiding said mixing means,
u. means for permitting air, after mixing, to enter said mixing vessel to eliminate vacuum trapped within said mixing vessel,
v. means for rotating the shaft of said driving motor, sufficiently slow, for less than 180 degrees, to make and/or ensure connection of said mixing means to said driving means,
w. conveyance means, which holds, supports, carries and guides:
  (1) a mixing unit,
  (2) said resilient support means, for said mixing unit,
  (3) said means for retracting said resilient support means,
  (4) said disposal means, for channeling washing liquid from said mixing vessel to a drain,
x. support and guidance means, for said conveyance means,
y. means for moving said conveyance means from load-unload position to mix-wash position and from mix-wash position to load-unload position,
z. means for releasing said resilient support means,
aa. means for holding and supporting all parts that are used in said apparatus to make the total said apparatus.

42. The mixer-washer apparatus set forth in claim 41 wherein said means for applying vacuum includes a vacuum reserve means, for rapidly sealing said lid to said mixing vessel and for quickly removing air and/or other gasses from said mixing vessel and from the materials being mixed.

43. A mixing unit comprising in combination:
a. a mixing vessel capable of easily being rotated and moved axially in a cylinder with the exterior circumferential surface of said mixing vessel being very close to the interior surface of said cylinder, for no wobbling or excessive radial movement to occur,
b. lid,
c. paddle, attached to a paddle shaft,
d. connector (part of means for connecting to a driving means), attached to said paddle shaft,
e. paddle shaft, extending through said lid, and sealed against passage of air or liquid, and capable of continuous or cyclic operation by said driving means,
f. bearing within a bearing housing, attached to said lid, for said paddle shaft,
g. channel means, through said lid, for passage of water and air,
h. tubing attached to said channel means,
i. means for sealing said mixing vessel and said lid together, for holding vacuum,
j. means, fixedly attached to a flange of said lid, for:
  (1) rotating and aligning said lid with a lid holding means, while said mixing vessel, or a portion thereof, is in said cylinder,
  (2) operating stationary electric switches during upward movement and during downward movement of said lid,
  (3) preventing lid from rotating while said lid is in a lid holding position,
k. washing liquid disposal means, attached to said mixing vessel,
l. washing liquid disposal means, attached to flange of said lid,
m. partial means for preventing rotation of said mixing vessel in the same rotational direction as the driving means, during mixing and during washing,
n. partial means for permitting rotation of said mixing vessel in the opposite said rotational direction, during said rotation of said lid, for said alignment, of said lid.

44. The mixing unit set forth in claim 43 wherein said partial means for preventing rotation of said mixing vessel in the same rotational direction as the driving means and partial means for permitting rotation of said mixing vessel in the opposite said rotational direction, is formed in the bottom exterior surface of said mixing vessel.

* * * * *